(12) United States Patent
Amarasinghe et al.

(10) Patent No.: US 7,897,770 B2
(45) Date of Patent: Mar. 1, 2011

(54) FLUORINATED DIHYDROTETRABENAZINE ETHER IMAGING AGENTS AND PROBES

(75) Inventors: Kande Kankanamalage Dayarathna Amarasinghe, Latham, NY (US); Michael James Rishel, Rensselaer, NY (US); Sean Richard Dinn, Delmar, NY (US); Bruce Fletcher Johnson, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 741 days.

(21) Appl. No.: 11/923,926

(22) Filed: Oct. 25, 2007

(65) Prior Publication Data

US 2009/0110636 A1 Apr. 30, 2009

(51) Int. Cl.
*C07D 455/06* (2006.01)
(52) U.S. Cl. ........................................ 546/95
(58) Field of Classification Search ............ 546/95
See application file for complete search history.

(56) References Cited

U.S. PATENT DOCUMENTS

| 2,843,591 A | 7/1958 | Brossi et al. |
| 4,193,998 A | 3/1980 | Szantay et al. |
| 5,278,308 A | 1/1994 | Kung |

FOREIGN PATENT DOCUMENTS

| DE | 1068261 B1 | | 11/1959 |
| WO | WO9316730 A1 | | 9/1993 |
| WO | WO 2005/077946 | * | 8/2005 |
| WO | WO2005077946 A1 | | 8/2005 |
| WO | WO2007005283 A2 | | 1/2007 |
| WO | WO2007130365 A2 | | 11/2007 |
| WO | WO2008154243 A1 | | 12/2008 |

OTHER PUBLICATIONS

PCT International Search Report dated Apr. 3, 2009.
Zheng et al., "Computational Neural Network Analysis of the Affinity of Lobeline and Tetrabenazine Analogs for the Vesicular Monoamine Transporter-2", Bioorganic & Medicinal Chemistry, vol. 15, pp. 2975-2992, 2007.
Popp et al., "Synthesis of Potential Antineoplastic Agents XXVI: 1,3,4,6,7,11b-Hexahydro-9,10-dimethoxy-2H-benso[a]2-quinolizinone Derivatives", Journal of Pharmaceutical Sciences, vol. 67, No. 6, pp. 871-873, XP-002513807, Jun. 1978.
PCT International Search Report dated Feb. 18, 2009.
Kung et al., "Characterization of Optically Resolved 9-Fluoropropyl-Dihydrotetrabenzaine as a Potential PET Imaging Agent Targeting Vesicular Monoamine Transporters", Nuclear Medicine and Biology, vol. 34, pp. 239-246, 2007.
Goswami et al., "Fluoroalkyl Derivatives of Dihydrotetrabenazine as Position Emission Tomography Imaging Agents Targeting Vesicular Monoamine Transporters", Nuclear Medicine and Biology, vol. 33, pp. 685-694, 2006.
Kilbourn et al., "Pharmacokinetics of [18F]Fluoroalkyl Derivatives of Dihyrotetrabenazine in Rate and Monkey Brain", Nuclear Medicine and Biology, vol. 34, pp. 233-237, 2007.

\* cited by examiner

*Primary Examiner*—Nizal S Chandrakumar
(74) *Attorney, Agent, or Firm*—Andrew J. Caruso

(57) ABSTRACT

The present invention provides novel fluorinated ether compounds having structure I

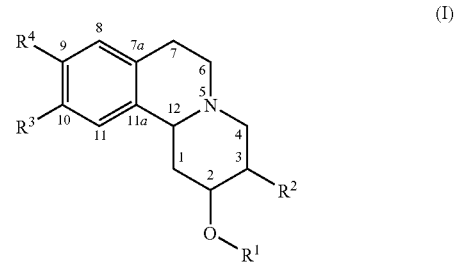

wherein $R^1$ is a $C_2$-$C_{10}$ fluorinated aliphatic radical; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical. The fluorinated ether compounds are provided in both racemic and enantiomerically enriched forms and may comprise either or both of fluorine-18 and fluorine 19. The fluorinated ether compounds are shown to possess high affinity for VMAT-2, a biomarker implicated in human diabetes. The fluorinated ether compounds comprising a fluorine-18 group are useful as PET imaging agents targeting the VMAT-2 biomarker. The non-radiolabeled fluorinated ether compounds are useful as probes for the discovery of PET imaging agents.

23 Claims, No Drawings

FLUORINATED DIHYDROTETRABENAZINE ETHER IMAGING AGENTS AND PROBES

CROSS REFERENCE TO RELATED APPLICATIONS

This application is related to U.S. patent application Ser. Nos. 11/760,359 and 11/760,372 filed on Jun. 8, 2007.

BACKGROUND

This invention relates to fluorinated ether compounds related to dihydrotetrabenazine and intermediates useful in the preparation of such fluorinated ether compounds.

Since first reported on in 1957 (Pletscher, A. (1957) Release of 5-hydroxytryptamine by benzoquinolizine derivatives with sedative action, *Science* 126, 507), tetrabenazine and structurally related compounds have been widely investigated, and a number of TBZ compounds and derivatives of tetrabenazine have shown promise in the treatment of a variety of conditions affecting human health. For example, dihydrotetrabenazine has been identified as an agent for the treatment of schizophrenia and other psychoses (See for example WO 2007017654 A1), and tetrabenazine has shown promise as an agent in the treatment of Huntington's disease (Neurology (2006), 66(3), 366-372). Although most preparations used in biological studies of tetrabenazine and its derivatives have been carried out on racemates, in at least one instance the biological activity exhibited by enantiomers tested separately was highly differentiated (See Koeppe, R. A. et al. (1999) Assessment of extrastriatal vesicular monoamine transporter binding site density using stereoisomers of [11C]dihydrotetrabenazine, *J Cereb Blood Flow Metab* 19, 1376-1384).

More recently, derivatives of 9-desmethyl(±)-dihydrotetrabenazine incorporating a fluorine-18 atom have been shown to be useful as PET imaging agents, *Nuclear Medicine and Biology* 33 (2006) 685-694. See also *Nuclear Medicine and Biology* 34 (2007) 239-246; and *Nuclear Medicine and Biology* 34 (2007) 233-237.

The present invention provides both a new class of fluorinated dihydrotetrabenazine derivatives and fluorinated dihydrotetrabenazine analogs and discloses efficient synthetic methodology which may be used to prepare such fluorinated ether compounds in enantiomerically enriched or racemic forms. The fluorinated ether compounds provided by the present invention are useful as PET imaging agents, probes for the development of PET imaging agents, and therapeutic agents. In addition, the present invention provides novel synthetic intermediate compositions which may be used to prepare either or both enantiomers of the subject dihydrotetrabenazine derivatives and dihydrotetrabenazine analogs.

BRIEF DESCRIPTION

In one embodiment, the present invention provides a fluorinated ether compound having structure I

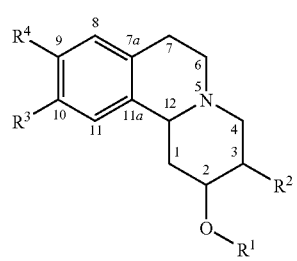

(I)

wherein $R^1$ is a $C_2$-$C_{10}$ fluorinated aliphatic radical; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

In another embodiment, the present invention provides an enantiomerically enriched fluorinated ether compound comprising a principal component enantiomer having structure II

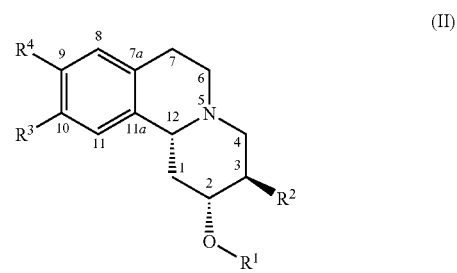

(II)

wherein $R^1$ is a $C_2$-$C_{10}$ fluorinated aliphatic radical; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

In yet another embodiment, the present invention provides an enantiomerically enriched fluorinated ether compound comprising a principal component enantiomer having structure III

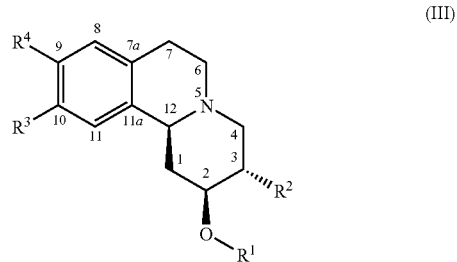

(III)

wherein $R^1$ is a $C_2$-$C_{10}$ fluorinated aliphatic radical; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

In yet another embodiment, the present invention provides a PET imaging agent comprising a fluorinated ether compound having structure I

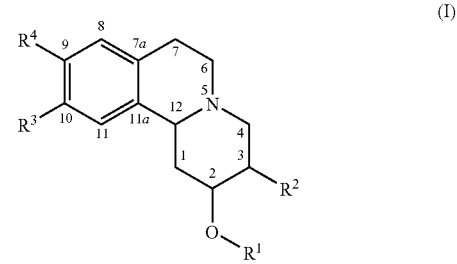

(I)

wherein $R^1$ is a $C_2$-$C_{10}$ fluorinated aliphatic radical comprising at least one fluorine-18 atom; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

DETAILED DESCRIPTION

In the following specification and the claims, which follow, reference will be made to a number of terms, which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "solvent" can refer to a single solvent or a mixture of solvents.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC($CF_3$)$_2$PhO—), 4-chloromethylphen-1-yl, 3-trifluorovinyl-2-thienyl, 3-trichloromethylphen-1-yl (i.e., 3-$CCl_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis (4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis (phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}$C(CF$_3$)$_2$ $C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$NC$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., —OC$_6$H$_{10}$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —O C$_6$H$_{10}$(CH$_2$)$_6$C$_6$H$_{10}$O—), 4-hydroxymethylcyclohex-1- yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$—), 4-methoxycyclohex-1-yl, 2-methoxycarbonylcyclohex-1-yloxy (2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)$_3$SiCH$_2$CH$_2$C$_6$H$_{10}$—), 4-vinylcyclohexen-1-yl, vinylidenebis (cyclohexyl), and the like. The term "a C$_3$-C$_{10}$ cycloaliphatic radical" includes cycloaliphatic radicals containing at least three but no more than 10 carbon atoms. The cycloaliphatic radical 2-tetrahydrofuranyl (C$_4$H$_7$O—) represents a C$_4$ cycloaliphatic radical. The cyclohexylmethyl radical (C$_6$H$_{11}$CH$_2$—) represents a C$_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a C$_6$ aliphatic radical comprising a methyl group, the methyl group being a functional group which is an alkyl group. Similarly, the 4-nitrobut-1-yl group is a C$_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e., —CHO), hexyl, hexamethylene, hydroxymethyl (i.e., —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilylpropyl (i.e., (CH$_3$O)$_3$SiCH$_2$CH$_2$CH$_2$—), vinyl, vinylidene, and the like. By way of further example, a C$_1$-C$_{10}$ aliphatic radical contains at least one but no more than 10 carbon atoms. A methyl group (i.e., CH$_3$—) is an example of a C$_1$ aliphatic radical. A decyl group (i.e., CH$_3$(CH$_2$)$_9$—) is an example of a C$_{10}$ aliphatic radical.

As noted, in one embodiment the present invention provides a fluorinated ether compound having structure I

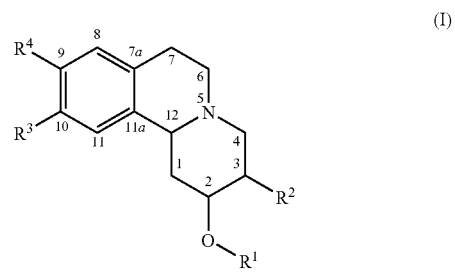

(I)

wherein R$^1$ is a C$_2$-C$_{10}$ fluorinated aliphatic radical; R$^2$ is a C$_1$-C$_{10}$ aliphatic radical, or a C$_3$-C$_{10}$ cycloaliphatic radical; R$^3$ is hydrogen or a C$_1$-C$_{10}$ aliphatic radical; and R$^4$ is hydrogen or a C$_1$-C$_{10}$ aliphatic radical.

The fluorinated ether compounds provided by the present invention are shown herein to possess a high affinity for Type 2 Vesicular Monoamine Transporters (VMAT-2) a group of biomarkers which are believed to correlate with diabetic activity in human patients. The discovery that substitution by fluorine is tolerated with respect to VMAT-2 binding in this series of novel fluorinated ether compounds enables the compounds of present invention to be used as positron emission tomography (PET) imaging agents in studies targeting the VMAT-2 biomarker.

Thus, in one embodiment, the present invention provides radiolabeled fluorinated ether compounds falling within the scope of generic structure I comprising a fluorine-18 atom, a radioactive positron emitting isotope of fluorine, which are suitable for use as imaging agents for positron emission tomography (PET) screening of human patients for pathological conditions related to diabetes. Positron emission tomography has become a medical imaging technique of critical importance to human health.

In an alternate embodiment, the present invention provides fluorinated ether compounds falling within the scope of generic structure I comprising a fluorine-19 atom, a stable isotope of fluorine. The fluorinated ether compounds comprising a fluorine-19 atom are useful in binding studies which allow the identification of those fluorinated ether compounds possessing optimal affinity for a target biomarker, for example VMAT-2. A substantial binding affinity of a given fluorine-19 containing fluorinated ether compound for a target biomarker such as VMAT-2 is a reliable predictor of utility in PET imaging of the corresponding fluorine-18 containing fluorinated ether compound. As is disclosed herein, fluorinated ether compounds having structure I show substantial binding affinity for VMAT-2.

Although throughout this disclosure the there is considerable focus on human health, the fluorinated ether compounds provided by the present invention are useful in the study and treatment of variety of human and animal diseases as imaging agents, as probes for the development of imaging agents, and as therapeutic agents.

Fluorinated ether compounds having structure I are illustrated in Table I below.

TABLE 1

Examples Of Fluorinated Ether Compounds Having Structure I

| Entry | R¹ | R² | R³ | R⁴ | Ring Position* Stereochemistry RP-2 | RP-3 | RP-12 |
|---|---|---|---|---|---|---|---|
| 1a | —CH₂CH₂-$^{19}$F | isobutyl | CH₃ | CH₃ | R/S | R/S | R/S |
| 1b | —CH₂CH₂-$^{18}$F | isobutyl | CH₃ | CH₃ | R | R | R |
| 1c | —CH₂CH₂CH₂-$^{19}$F | isobutyl | CH₃O | CH₃O | R/S | R/S | R/S |
| 1d | —CH₂CH₂CH₂-$^{18}$F | isobutyl | CH₃O | CH₃O | S | S | S |
| 1e | —CH₂CH₂CH₂CH₂-$^{19}$F | neopentyl | EtO | CH₃O | R | S | R |
| 1f | —CH₂CH₂CH₂CH₂-$^{18}$F | cyclopropylmethyl | EtO | EtO | S | R | S |
| 1g | —CH₂CH₂OCH₂CH₂-$^{19}$F | cyclopentylmethyl | CH₃CH₂ | CH₃CH₂ | R/S | R/S | R/S |
| 1h | —CH₂CH₂OCH₂CH₂-$^{18}$F | isopentyl | CH₃O | CH₃O | R | R | R |
| 1i | —CH₂CH(OH)CH₂-$^{18}$F | isobutyl | CH₃O | CH₃O | R/S | R/S | R/S |
| 1j | —CH₂CH($^{18}$F)CH₂-$^{18}$F | isobutyl | CH₃O | CH₃O | R/S | R/S | R/S |
| 1k | —CH₂C(O)CH₂-$^{18}$F | isobutyl | CH₃O | CH₃O | R | R | R |

*RP-2 = Ring position-2,
RP-3 = Ring position-3,
RP-12 = Ring position-12

In general, and throughout this disclosure, where no absolute or relative stereochemistry is shown for a structure, as in for example structure I, the structure is intended to encompass all possible absolute and relative stereochemical configurations. Thus, structure I depicts a fluorinated ether compound in which no absolute or relative stereochemistry is shown. As such, structure I is intended to represent a genus of fluorinated ether compounds which includes the racemic fluorinated ether compound 1a (Table 1) having both the R configuration and S configuration at ring positions-2, 3 and 12. In another embodiment, structure I represents fluorinated ether compound 1b (Table 1) having the R configuration (absolute stereochemistry) at ring positions-2, 3 and 12. In yet another embodiment, structure I represents fluorinated ether compound 1d (Table 1) having absolute stereochemistry opposite that of fluorinated ether compound 1b. Those having ordinary skill in the art will appreciate that the individual fluorinated ether compounds shown in Table 1 herein are illustrative of dihydrotetrabenazine (DTBZ) ether derivatives falling within the scope of generic structure I.

As noted, in one embodiment, the present invention provides a fluorinated ether compound having structure I which may be a racemic mixture (e.g. fluorinated ether compound 1a (Table 1), a single enantiomer (e.g. fluorinated ether compound 1b (Table 1), or a composition enantiomerically enriched in a single principal component enantiomer. Entries 2a-2c in Table 2 below illustrate fluorinated ether compounds comprising a principal component enantiomer and at least one minor component enantiomer.

TABLE 2

Fluorinated Ether Compounds Comprising A Principal Component Enantiomer And At Least One Minor Component Enantiomer.

| Entry | Structure of Principal Component Enantiomer | Structure of Minor Component(s) |
|---|---|---|
| 2a | [structure with H$_3$CO, H$_3$CO substituents, positions 12, 2(R), 3(R), R, O-CH$_2$-CH$_2$-$^{18}$F]<br>96 mole % | [structure with H$_3$CO, H$_3$CO substituents, positions 12, 2(S), 3(S), S, O-CH$_2$-CH$_2$-$^{18}$F] |
| 2b | [structure with EtO, positions 12, 2(R), 3(R), R, O-CH$_2$-CH=CH-$^{19}$F]<br>98 mole % | [structure with EtO, positions 12, 2(S), 3(S), S, O-CH$_2$-CH=CH-$^{19}$F] |
| 2c | [structure with EtO, positions 12, 2(R), 3(R), R, O-CH$_2$-C(=O)-CH$_2$-$^{18}$F]<br>88 mole % | [structure with EtO, positions 12, 2(S), 3(S), S, O-CH$_2$-C(=O)-CH$_2$-$^{18}$F] +<br><br>[structure with EtO, positions 12(R), 2(S), 3(R), O-CH$_2$-C(=O)-CH$_2$-$^{18}$F] +<br><br>[structure with EtO, positions 12(S), 2(R), 3(S), O-CH$_2$-C(=O)-CH$_2$-$^{18}$F] |

In Table 2 the fluorinated ether compositions comprise a principal component enantiomer (the structures appearing under the title heading "Structure of Principal Component Enantiomer") and one or more "Minor Components". In the fluorinated ether compositions illustrated in Table 2 the mole percentage of the principal component enantiomer is given as "mole %" and refers to the mole percentage of the principal component enantiomer having the structure shown relative to the amounts of all other dihydrotetrabenazine ether components in the composition. For the purposes of this discussion a dihydrotetrabenazine ether derivative is any compound falling within the scope of generic structure I. Entry 2a is a fluorinated ether composition comprising 96 mole % of the R, R, R principal component enantiomer shown and a lesser amount of the S, S, S minor component enantiomer. Entry 2c is a fluorinated ether composition comprising a principal component enantiomer having the structure shown and three minor components having structures shown. Those skilled in the art will appreciate that the composition illustrated in Entry 2c of Table 2 represents an example of a diastereomeric mixture.

In one embodiment, the present invention provides a fluorinated ether compound represented by structure I which is enantiomerically enriched and is comprised of at least 95 mole percent (mole %) of an enantiomer having the R configuration at ring position-12.

In an alternate embodiment, the present invention provides a fluorinated ether compound represented by structure I which is enantiomerically enriched and is comprised of at least 95 mole percent (mole %) of an enantiomer having the R configuration at ring position-3.

In one embodiment, the present invention provides a fluorinated ether compound having structure I in which the fluorinated ether moiety at ring position-2 (—O—$R^1$) has an anti configuration relative to the group $R^2$ at ring position-3. The principal component enantiomers of Entries 2a-2c of Table 2 illustrate fluorinated ether compounds in which the fluorinated ether moiety at ring position-2 (—O—$R^1$) has an anti configuration relative to the group $R^2$ at ring position-3. Entry 1a of Table 1 represents a racemic fluorinated ether compound in which each of the component enantiomers is characterized by an anti-relationship between the fluorinated ether moiety at ring position-2 and the group $R^2$ at ring position-3.

In one embodiment, the present invention provides an enantiomerically enriched fluorinated ether compound comprising a principal component enantiomer having structure II

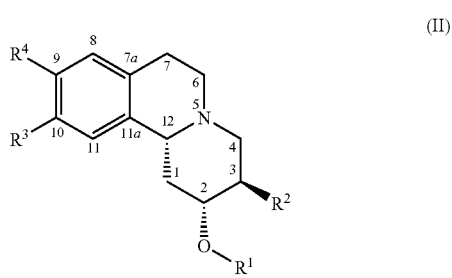

(II)

wherein $R^1$ is a $C_2$-$C_{10}$ fluorinated aliphatic radical; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

Principal component enantiomers having structure II are illustrated in Table 3 below.

TABLE 3

Principal Component Enantiomers Having Structure II

| Entry | Structure |
|---|---|
| 3a | H$_3$CO, CH$_3$CH$_2$O structure with $^{19}$F |
| 3b | H$_3$C-CH$_2$ structure with $^{18}$F |
| 3c | H$_3$C, H$_3$C structure with $^{18}$F |

In one embodiment, the present invention provides an enantiomerically enriched fluorinated ether compound comprising at least 80 mole percent of an enantiomer having structure II, for example a fluorinated ether composition comprising the compound of Entry 3a (Table 2) wherein the R, R, R enantiomer shown represents at least 80 mole percent relative to the amounts of all other dihydrotetrabenazine ether components in the composition.

In an alternate embodiment, the present invention provides an enantiomerically enriched fluorinated ether compound which is comprised of at least 95 mole % of an enantiomer having structure II, for example a fluorinated ether composition comprising the compound of Entry 3b (Table 2) wherein the R, R, R enantiomer shown represents at least 95 mole percent relative to the amounts of all other dihydrotetrabenazine ether components in the composition.

In one embodiment, the present invention provides an enantiomerically enriched fluorinated ether compound comprising a principal component enantiomer having structure II wherein $R^1$ is a $C_2$-$C_{10}$ fluorinated aliphatic radical; $R^2$ is isobutyl; and $R^3$ and $R^4$ are methoxy groups and which are illustrated in Table 4 below.

TABLE 4

Principal Component Enantiomers Having Structure II
Wherein R¹ Is A $C_2$-$C_{10}$ Fluorinated Aliphatic
Radical; R² Is Isobutyl; And R³ And R⁴ Are Methoxy
Groups

| Entry | Structure |
|---|---|
| 4a | 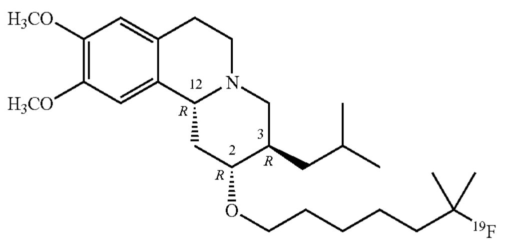 |
| 4b | 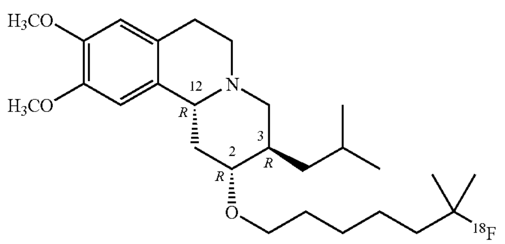 |
| 4c | 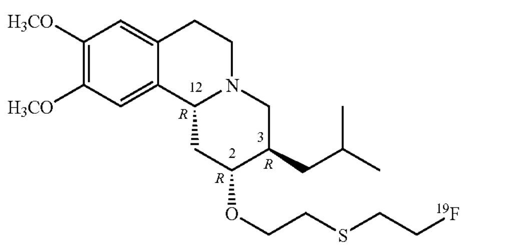 |
| 4d | 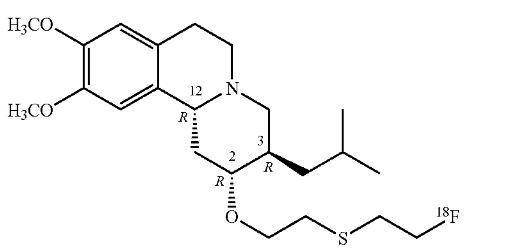 |

In one embodiment, the present invention provides an enantiomerically enriched fluorinated ether compound comprising a principal component enantiomer having structure III (III)

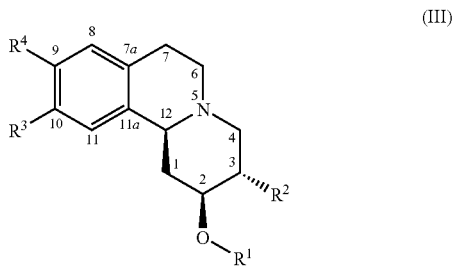

wherein R¹ is a $C_2$-$C_{10}$ fluorinated aliphatic radical; R² is a $C_1$-$C_{10}$ aliphatic radical, or a $C_3$-$C_{10}$ cycloaliphatic radical; R³ is hydrogen or a $C_1$-$C_{10}$ aliphatic radical; and R⁴ is hydrogen or a $C_1$-$C_{10}$ aliphatic radical.

Principal component enantiomers having structure III are illustrated in Table 5 below.

TABLE 5

Principal Component Enantiomers Having Structure III

| Entry | Structure |
|---|---|
| 5a | 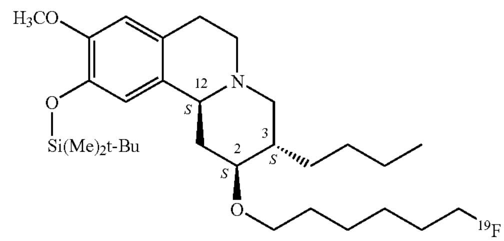 |
| 5b | 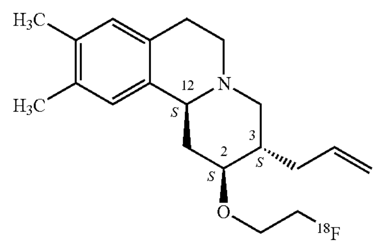 |
| 5c | 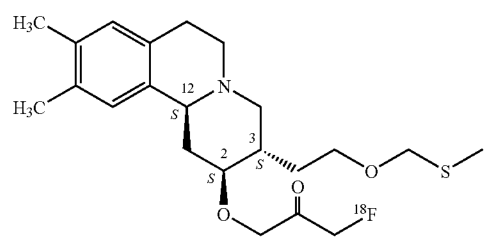 |

In one embodiment, the present invention provides an enantiomerically enriched fluorinated ether compound comprising at least 80 mole percent of an enantiomer having structure III, for example a fluorinated ether composition comprising the compound of Entry 5a (Table 5) wherein the S, S, S enantiomer shown represents at least 80 mole percent relative to the amounts of all other dihydrotetrabenazine ether components in the composition. In another embodiment, the present invention provides an enantiomerically enriched fluorinated ether compound comprising at least 95 mole percent of an enantiomer having structure III, for example a fluorinated ether composition comprising the compound of Entry 5b (Table 5) wherein the S, S, S enantiomer shown represents at least 95 mole percent relative to the amounts of all other dihydrotetrabenazine ether components in the composition.

In another embodiment, the present invention provides an enantiomerically enriched fluorinated ether compound comprising a principal component enantiomer having structure III wherein R¹ is a $C_2$-$C_{10}$ fluorinated aliphatic radical; R² is isobutyl; and R³ and R⁴ are methoxy groups, and which are illustrated in Table 6 below.

TABLE 6

Principal Component Enantiomers Having Structure III
Wherein $R^1$ Is A $C_2$-$C_{10}$ Fluorinated Aliphatic
Radical; $R^2$ Is Isobutyl; And $R^3$ And $R^4$ Are Methoxy
Groups Entry Structure 6a 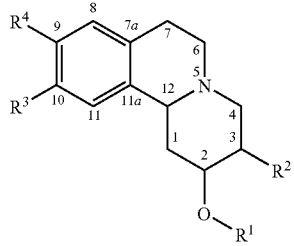

6b

6c 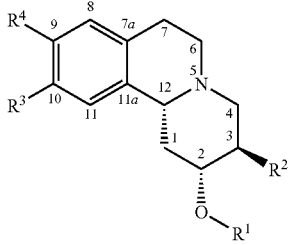

6d

As noted, the fluorinated ether compounds I, II and III provided by the present invention may comprise a fluorine-18 atom in the fluorinated ether moiety —$OR^1$. In various embodiments such fluorinated ether compounds comprising a fluorine-18 atom are useful as PET imaging agents. Thus, in one embodiment, the present invention provides a PET imaging agent comprising a fluorinated ether compound having structure I

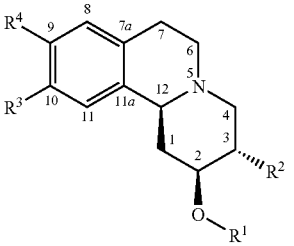

(I)

wherein $R^1$ is a $C_2$-$C_{10}$ fluorinated aliphatic radical comprising at least one fluorine-18 atom; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

In another embodiment, the present invention provides a PET imaging agent comprising an enantiomerically enriched fluorinated ether compound comprising a principal component enantiomer having structure II (II)

wherein $R^1$ is a $C_2$-$C_{10}$ fluorinated aliphatic radical comprising at least one fluorine-18 atom; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

In yet another embodiment, the present invention provides a PET imaging agent comprising an enantiomerically enriched fluorinated ether compound comprising a principal component enantiomer having structure III (III)

wherein $R^1$ is a $C_2$-$C_{10}$ fluorinated aliphatic radical comprising at least one fluorine-18 atom; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

The term "PET imaging agent" as used herein refers to a composition comprising a fluorine-18 labeled fluorinated ether compound which may be administered to a patient in order to perform a PET scan. Typically, the imaging agent is presented to the patient in the form of an aqueous formulation containing a sufficient amount of fluorine-18 labeled fluorinated ether compound to conduct the PET scan. Typically, the amount of fluorine-18 labeled fluorinated ether compound presented to a patient corresponds to a weight of the fluorine-18 labeled fluorinated ether compound on the order of nanograms. In reference to the relative amounts of non-radioactive fluorine-19 containing fluorinated ether compound present in the PET imaging agent presented to a patient, the PET imaging agent typically has a specific activity in a range from about 1 to about 99 percent. In one embodiment, the PET imaging agent has a specific activity in a range from about 10 to about 95 percent. In another embodiment, the PET imaging agent has a specific activity in a range from about 20 to about 90 percent.

The aqueous formulation containing the fluorine-18 fluorinated ether compound is typically administered intravenously and may contain various agents which promote the dispersal of the PET imaging agent in water. In one embodiment, the PET imagining agent may be administered to a patient in an aqueous formulation comprising ethanol and the fluorine-18 labeled fluorinated ether compound. In an alternate embodiment, the PET imagining agent may be administered to a patient as an aqueous formulation comprising dextrose and the fluorine-18 labeled fluorinated ether compound. In yet another embodiment, the PET imagining agent may be administered to a patient as an aqueous formulation comprising saline and the fluorine-18 labeled fluorinated ether compound.

In one embodiment, the present invention provides a PET imaging agent comprising a fluorinated ether compound having structure IV.

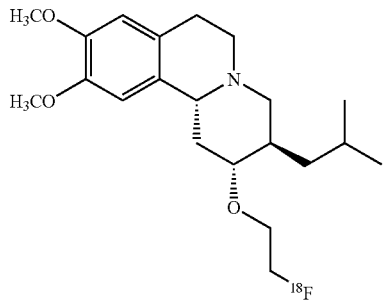

(IV)

In addition to being useful as PET imaging agents and as probes for determining the suitability of a given fluorinated ether compound for use as a PET imaging agent, the fluorinated ether compounds provided by the present invention are believed to possess therapeutic utility in the treatment of diseases such as schizophrenia and Huntington's disease. Thus, in one embodiment, the present invention provides a fluorinated ether compound having structure I which is useful in treating a pathological condition in a patient. In another embodiment, the present invention provides an enantiomerically enriched fluorinated ether compound having structure II which is useful in treating a pathological condition in a patient. In yet another embodiment, the present invention provides an enantiomerically enriched fluorinated ether compound having structure III which is useful in treating a pathological condition in a patient. Typically the amount of the fluorinated ether compound administered to a patient is on the order of milligrams.

Those skilled in the art will appreciate that fluorinated ether compounds such as fluorinated ether compounds falling within the scope of generic structure I, or generic structures II or III may under a variety of conditions form salts which are useful as PET imaging agents, probes for the discovery and development of imaging agents, and/or as therapeutic agents. Thus, the present invention provides a host of novel and useful fluorinated ether compounds and their salts. For example, in one particular embodiment, the present invention provides the hydrochloride salt of the novel fluorinated ether compound having structure IV.

The fluorinated ether compounds of the present invention may be prepared by a variety of methods including those provided in the experimental section of this disclosure. In one embodiment, the fluorinated ether compound is prepared by reaction of a dihydrotetrabenazine having structure V

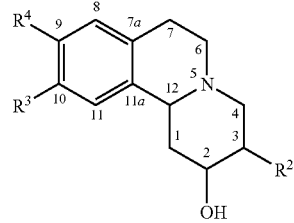

(V)

wherein $R^2$ is a $C_1$-$C_{10}$ aliphatic radical, or a $C_3$-$C_{10}$ cycloaliphatic radical; $R^3$ hydrogen or is a $C_1$-$C_{10}$ aliphatic radical; and $R^4$ is hydrogen or a $C_1$-$C_{10}$ aliphatic radical;

with a difunctional electrophile to produce a first intermediate dihydrotetrabenazine compound which is itself susceptible to reaction with nucleophilic fluoride ion or an electrophilic fluorinating agent, or which may be transformed via one or more chemical steps into a second intermediate dihydrotetrabenazine compound which is susceptible to reaction with nucleophilic fluoride ion or an electrophilic fluorinating agent.

Thus in one embodiment, the present invention provides a fluorophilic compound having structure VI

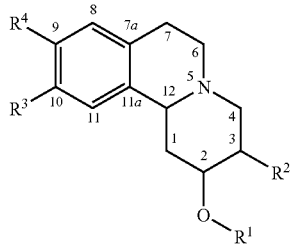

(VI)

wherein $R^1$ is a $C_2$-$C_{20}$ aliphatic, a $C_3$-$C_{20}$ cycloaliphatic, or a $C_3$-$C_{20}$ aromatic radical comprising at least one functional group susceptible to reaction with nucleophilic fluoride ion or an electrophilic fluorinating agent; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

Fluorophilic compounds having structure VI are illustrated in Table 7 below.

TABLE 7

Fluorophilic Compounds Having Structure VI

| Entry | R¹ | R² | R³ | R⁴ | Ring Position* Stereochemistry RP-2 | RP-3 | RP-12 |
|---|---|---|---|---|---|---|---|
| 7a | –CH₂CH₂–OTs | isobutyl | $CH_3$ | $CH_3$ | R/S | R/S | R/S |
| 7b | –CH₂CH₂–O–SO₂CF₃ | isobutyl | $CH_3$ | $CH_3$ | R | R | R |
| 7c | –CH₂CH₂CH₂–O–C(O)–C₆H₄–NO₂ (para) | isobutyl | $CH_3O$ | $CH_3O$ | R/S | R/S | R/S |
| 7d | –CH₂CH₂–OSO₂CH₃ | isobutyl | $CH_3O$ | $CH_3O$ | S | S | S |
| 7e | –CH₂C≡CH | isobutyl | EtO | $CH_3O$ | R | S | R |
| 7f | –CH₂CH=CHCH₃ | cyclopropyl | EtO | EtO | S | R | S |
| 7g | –C(=CH₂)(OMe) | cyclopentyl | $CH_3CH_2$ | $CH_3CH_2$ | R/S | R/S | R/S |
| 7h | –C(=CH₂)(OMe) | isobutyl | $CH_3O$ | $CH_3O$ | R | R | R |
| 7i | –CH₂–(epoxide) | isobutyl | $CH_3O$ | $CH_3O$ | R/S | R/S | R/S |
| 7j | –CH₂–C(O)–CH₂–OTs | isobutyl | $CH_3O$ | $CH_3O$ | R/S | R/S | R/S |
| 7k | –CH₂–C(=CH₂)–CH₂–OTs | isobutyl | $CH_3O$ | $CH_3O$ | R | R | R |
| 7l | cyclic sulfate (1,3,2-dioxathiolane 2,2-dioxide) | isobutyl | $CH_3O$ | $CH_3O$ | R | R | R |

The fluorophilic compounds provided by the present invention include both racemic mixtures, for example the compositions of Entries 7a, 7c, 7g, 7i, and 7j; and enantiomerically enriched compositions, for example a composition comprising a principal component enantiomer having the structure shown in Entry 7b.

In one embodiment, the present invention provides a fluorophilic compound having structure VI, wherein R¹ is a $C_2$-$C_{20}$ aliphatic radical, a $C_3$-$C_{20}$ cycloaliphatic radical, or a $C_3$-$C_{20}$ aromatic radical comprising at least one functional group susceptible to reaction with nucleophilic fluoride ion.

In one embodiment, the functional group susceptible to reaction with nucleophilic fluoride ion is an aromatic sulfonate ester (e.g. tosylate, benzenesulfonate, naphthalenesulfonate). In an alternate embodiment, the functional group susceptible to reaction with nucleophilic fluoride ion is an aliphatic sulfonate ester (e.g. methane sulfonate, trifluoromethane sulfonate).

In one embodiment, the functional group susceptible to reaction with nucleophilic fluoride ion is selected from the group consisting of tosylate, mesylate, trifluoromethane sulfonate, and p-nitrobenzoate groups.

In one embodiment, the present invention provides a fluorophilic compound having structure VI wherein the group $R^1$ comprises at least one tosylate group susceptible to reaction with nucleophilic fluoride ion. See for example the Entries 7a, 7j and 7k of Table 7. As defined herein, the tosylate group is an aromatic radical and the group $R^1$ comprising the tosylate group is also an aromatic radical. In the compound shown in Entry 7a for example, the group $R^1$ comprising the tosylate group is a $C_9$ aromatic radical which upon displacement with fluoride ion becomes a $C_2$ fluorinated aliphatic radical.

In an alternate embodiment, the present invention provides a fluorophilic compound having structure VI wherein the group $R^1$ comprises at least one mesylate group susceptible to reaction with nucleophilic fluoride ion. As defined herein, the mesylate group is an aliphatic radical and the group $R^1$ comprising the mesylate group may be an aliphatic, a cycloaliphatic or an aromatic radical depending on the overall structure of the group $R^1$. For example, in a fluorophilic compound having structure VI in which $R^1$ comprises both a mesylate group and an epoxy group, the group $R^1$ is a cycloaliphatic radical. Alternatively, in a fluorophilic compound having structure VI in which $R^1$ comprises both a mesylate group and a tosylate group, the group $R^1$ is an aromatic radical. It is helpful to bear in mind that the definitions of aliphatic, cycloaliphatic and aromatic radicals provided in this disclosure establish a hierarchy in which aliphatic radicals (non-cyclic arrays of atom(s)) must be free of cycloaliphatic groups (a cyclic array of atoms which is not aromatic) and aromatic groups (a cyclic array of atoms which is aromatic), cycloaliphatic radicals must be free of aromatic groups, and aromatic radicals must simply comprise an aromatic group.

In an alternate embodiment, the present invention provides a fluorophilic compound having structure VI wherein the group $R^1$ comprises at least one trifluoromethane sulfonate (triflate) group susceptible to reaction with nucleophilic fluoride ion. See for example Entry 7b of Table 7.

In an alternate embodiment, the present invention provides a fluorophilic compound having structure VI wherein the group $R^1$ comprises at least one p-nitrobenzoate group susceptible to reaction with nucleophilic fluoride ion. See for example Entry 7c of Table 7.

In an alternate embodiment, the present invention provides a fluorophilic compound having structure VI wherein the group $R^1$ comprises at least one methane sulfonate group susceptible to reaction with nucleophilic fluoride ion. See for example Entry 7d of Table 7.

In an alternate embodiment, the present invention provides a fluorophilic compound having structure VI wherein the group $R^1$ comprises at least one epoxy group susceptible to reaction with nucleophilic fluoride ion. See for example Entry 7l of Table 7.

In yet another embodiment, the present invention provides a fluorophilic compound having structure VI wherein the group $R^1$ comprises at least one cyclic sulfate group susceptible to reaction with nucleophilic fluoride ion. See for example Entry 7l of Table 7.

In one embodiment, the present invention provides a fluorophilic compound having structure VI, wherein $R^1$ is a $C_2$-$C_{20}$ aliphatic radical comprising at least one functional group susceptible to reaction with an electrophilic fluorinating agent, for example fluorine gas, perchloryl fluoride, mercuric fluoride, and phenyl selenenyl fluoride.

Thus in one embodiment, the functional group susceptible to reaction with an electrophilic fluorinating agent is selected from the group consisting of carbon-carbon double bonds and carbon-carbon triple bonds. Entries 7e, 7f, 7g and 7h of Table 7 illustrate compounds falling within the scope of generic structure VI which are susceptible to reaction with an electrophilic fluorinating agent.

Fluorophilic tetrabenazine compounds VI may be prepared in enantiomerically enriched or racemic forms. For example, a fluorophilic tetrabenazine compound VI may be enriched in the R, R, R-enantiomer shown in Entry 7b of Table 7. Alternatively, a fluorophilic tetrabenazine compound may be enriched in an enantiomer having absolute stereochemistry opposite that of Entry 7b of Table 7, for example the S,S,S-enantiomer of Entry 7d.

Thus, in one embodiment, the present invention provides an enantiomerically enriched fluorophilic compound comprising a principal component enantiomer having structure VII

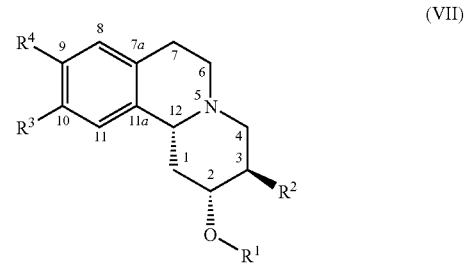

wherein $R^1$ is a $C_2$-$C_{20}$ aliphatic, a $C_3$-$C_{20}$ cycloaliphatic, or a $C_3$-$C_{20}$ aromatic radical comprising at least one functional group susceptible to reaction with nucleophilic fluoride ion or an electrophilic fluorinating agent; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical. Principal component enantiomers VII are illustrated by Entries 7b, 7e, 7h, 7k, and 7l of Table 7.

In an alternate embodiment, the present invention provides an enantiomerically enriched fluorophilic compound comprising a principal component enantiomer having structure VIII

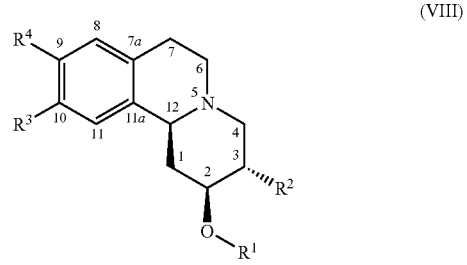

wherein $R^1$ is a $C_2$-$C_{20}$ aliphatic, a $C_3$-$C_{20}$ cycloaliphatic, or a $C_3$-$C_{20}$ aromatic radical comprising at least one functional group susceptible to reaction with nucleophilic fluoride ion or an electrophilic fluorinating agent; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical. Principal component enantiomers VIII are illustrated by Entry 7d of Table 7.

Dihydrotetrabenazine compounds having structure V are readily prepared from the corresponding tetrabenazine (TBZ) having structure IX

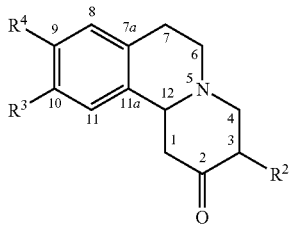

(IX)

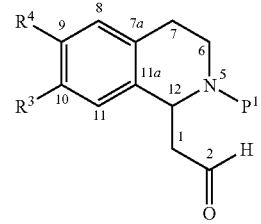

(X)

wherein $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical. For example, reduction of the carbonyl group at ring position-2 with sodium borohydride in ethanol affords dihydrotetrabenazine V.

Tetrabenazine compounds having structure IX are known in the chemical literature, and the preparation of both racemic and enantiomerically enriched tetrabenazine and dihydrotetrabenazine compositions have been described. Co-pending U.S. patent application Ser. No. 11/760,359 and Ser. No. 11/760,372 filed Jun. 8, 2007 disclose methods for the preparation of racemic and enantiomerically enriched tetrabenazine compositions. In addition, the Examples Section of the present disclosure provides detailed experimental descriptions of the preparation and characterization of tetrabenazine compounds Ix and dihydrotetrabenazine compounds V.

In general, tetrabenazine compounds IX can be prepared by reacting a nucleophilic alkenyl species with an aldehyde compound having structure X wherein $R^3$ is hydrogen or a $C_1$-$C_{20}$ aliphatic radical; and $R^4$ is hydrogen or a $C_1$-$C_{20}$ aliphatic radical; and $P^1$ is a protecting group, to provide an allylic alcohol (See Methods 4, 5, and 6 of the Examples section), which is then oxidized to provide an enone designated the "first intermediate" (See Methods 7, 8, and 9 of the Examples section), the protecting group of which is then removed and the resultant deprotected first intermediate undergoes an amino cyclization reaction to afford the corresponding TBZ compound.

Representative aldehyde compounds encompassed by generic formula X are given in Table 8.

TABLE 8

Representative Aldehyde Compounds Encompassed By Formula X

| Entry | Compound Type | Ring Position* Stereo-chemistry | Structure |
|---|---|---|---|
| 8a | Single "R" enantiomer, "Boc" protecting group $P^1$ | RP-12 "R" | 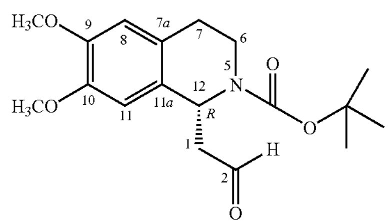 |
| 8b | Single "S" enantiomer, "Boc" protecting group $P^1$ | RP-12 "S" | 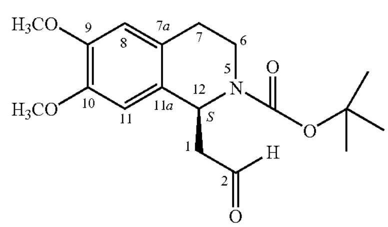 |
| 8c | Enantiomerically enriched mixture of "R" and "S" enantiomers, "alloc" protecting group $P^1$ | RP-12 "R/S" | 95%    5% |

TABLE 8-continued

Representative Aldehyde Compounds Encompassed By Formula X

| Entry | Compound Type | Ring Position* Stereo-chemistry | Structure |
|---|---|---|---|
| 8d | Racemic mixture of "R" and "S" enantiomers; "Fmoc" protecting group $P^1$ | RP-12 "R/S" | 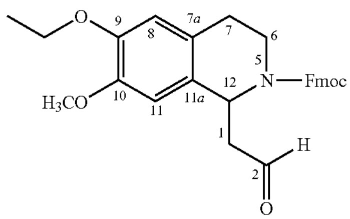 |
| 8e | Racemic mixture of "R" and "S" enantiomers; "Cbz" protecting group $P^1$ | RP-12 "R/S" | 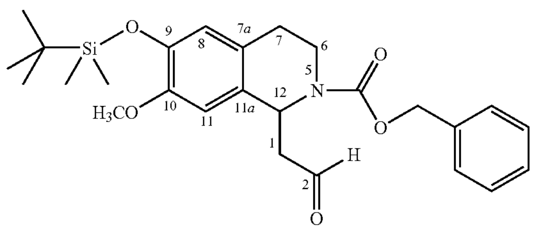 |
| 8f | Racemic mixture of "R" and "S" enantiomers; "Teoc" protecting group $P^1$ | RP-12 "R/S" | 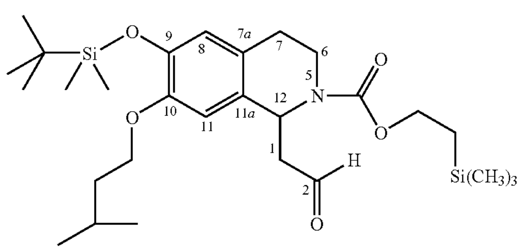 |
| 8g | Single "R" enantiomer, "Boc" protecting group $P^1$ | RP-12 "R" | 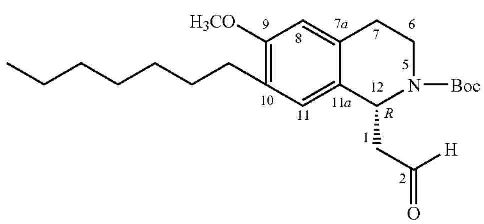 |

The preparation of the aldehyde compound featured in Entry 8a of Table 8 is described in the Examples section of this disclosure (Methods 1-3). In general, the class of aldehyde compounds represented by structure X may be prepared by art recognized methods, for example using the methodology depicted in Scheme 1.

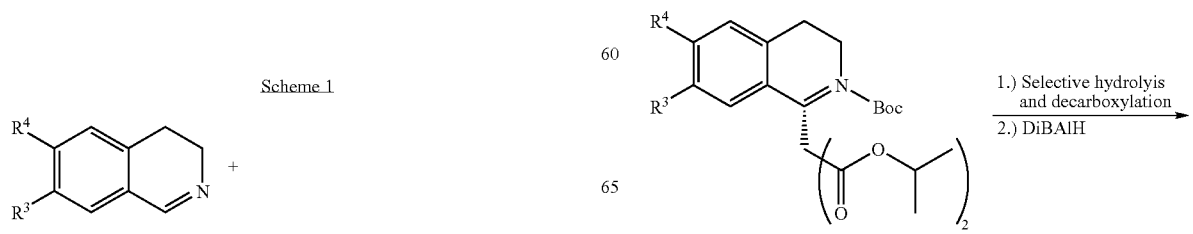

-continued

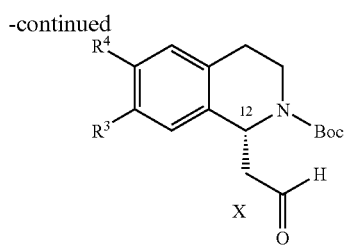

Thus, Aldehyde compounds X may be prepared from intermediates prepared using methodology described by Sasamoto et al. (Journal of the American Chemical Society 128, 14010-14011, 2006). Sasamoto et al. disclose the preparation of enantiomerically enriched tetrahydroquinoline malonate compounds which may be converted as shown in the present disclosure to aldehyde compound X by selective hydrolysis of one of the ester moieties of the tetrahydroquinoline malonate and decarboxylation followed by reduction of the resultant tetrahydroisoquinoline monoester to aldehyde compound X as depicted in Scheme 1.

One of ordinary skill in the art will appreciate that the 2 mole percent DM-SEGPHOS shown in Scheme 1 represents a chiral catalyst responsible for the enantiomeric enrichment of the product aldehyde X, and further that the use of DM-SEGPHOS of opposite chirality as the chiral catalyst will afford a product aldehyde X enantiomerically enriched in the "S" enantiomer (aldehyde compound X having the S configuration at ring position-12 (See for example Entry 8b of Table 8). Suitable chiral catalysts include those disclosed by Sasamoto et al. (Journal of the American Chemical Society 128, 14010-14011, 2006), for example (S)-Binap, (R)-Binap, (S)-DM-Binap, (R)-DM-Binap, (S)-DM-SEGPHOS, and (R)-DM-SEGPHOS. Typically use of a catalyst consisting of a ligand possessing a single, for example "S", configuration produces stereochemically enriched malonate adducts of the opposite "R" configuration and vice versa.

In addition to the use of a chiral catalyst to generate aldehyde compounds X enriched in a single configuration at ring position-12, there are available a wide variety of methods for the separation of racemic aldehyde X into its constituent enantiomers. For example, racemic aldehyde compound X may be separated into its constituent enantiomers by high performance liquid chromatography (hplc) on a chiral hplc column.

Other methods for producing enantiomerically enriched compositions provided by the present invention include conversion of a racemic fluorinated ether compound having structure I compound into an adduct comprising a mixture of diastereomers which are then separated by fractional crystallization. For example, a racemic fluorinated ether compound having structure I may be reacted with (−)-tartaric acid to form an adduct (ammonium tartarate salt) of the racemic fluorinated ether compound, said adduct comprising a mixture of diastereomeric ammonium tartarate salts which are then separated by fractional crystallization.

EXAMPLES

The following examples are intended only to illustrate methods and embodiments in accordance with the invention, and as such should not be construed as imposing limitations upon the claims.

Methods for Preparing Dihydrotetrrabenazine (DTBZ) Starting Materials

Method 1 Preparation of Protected Diester 2

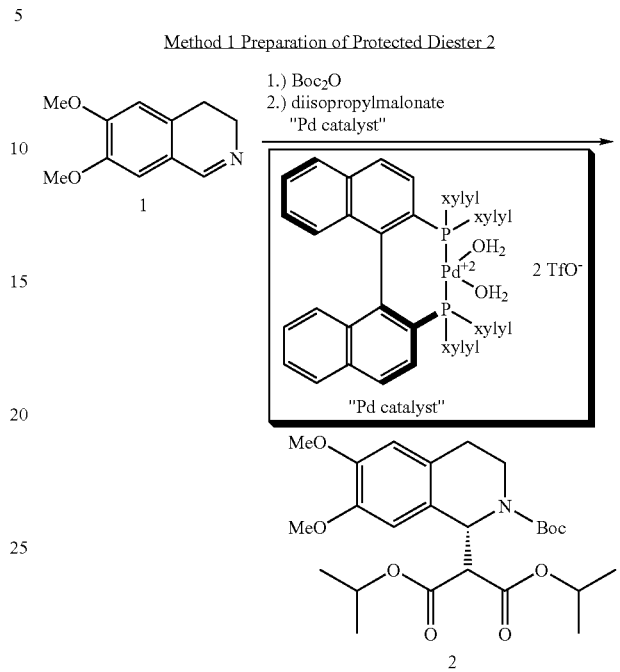

The dihydroisoquinoline 1 (1.0 eq.) and Boc anhydride (1.5 eq.) were dissolved in $CH_2Cl_2$ at room temperature to provide a 1.5 M solution with respect to the dihydroisoquinoline. The mixture was allowed to stir for 30 min. Following the allotted time, the reaction mixture was cooled to 0° C. and then diisopropylmalonate (1.5 eq.) followed by a pre-chilled solution of the Pd catalyst (0.008 eq.) in dichloromethane were added successively to the reaction mixture to provide a final reaction concentration of 0.84 M with respect to the starting dihydroisoquinoline. The reaction mixture was allowed to continue stirring at ~2.5° C. for 15 h. Following this time EtOAc and brine were added to the reaction mixture. The aqueous layer was extracted with three portions of EtOAc and the combined organic layers were dried ($Na_2SO_4$), filtered, and concentrated under reduced pressure to provide the crude product. The crude material was dissolved in a minimal amount of dichloromethane and purified by flash chromatography on $SiO_2$ (15-30% EtOAc-hexanes, elution was observed at 285 nm and 228 nm). The product 2 was a colorless solid that existed as a mixture of rotamers in solution at room temperature 94%: $[\alpha]^{26}_D$ −69.0 (c 0.21, $CHCl_3$); $^1H$ NMR ($CDCl_3$) δ 0.81-1.02 (m, 6H), 1.06-1.17 (m, 6H), 1.23-1.38 (m, 9H), 2.51-2.63 (m, 1H), 2.64-2.77 (m, 1H), 3.20-3.29 (m, 0.6H), 3.32-3.41 (m, 0.4H), 3.51-3.58 (m, 1H), 3.62-3.70 (m, 6H), 3.70-3.76 (m, 0.4H), 3.91-4.01 (m, 0.6H), 4.65-4.82 (m, 1H), 4.83-4.98 (m, 1H), 5.71 (apparent d, J=5.7 Hz, 0.6H), 5.78 (apparent d, J=7.9 Hz, 0.4H), 6.42-6.49 (m, 1H), 6.77 (s, 0.6H), 6.81 (s, 0.4H); $^{13}C$ NMR ($CDCl_3$) δ 21.02, 21.09, 21.18, 21.32, 27.24, 27.95, 28.02, 37.60, 39.34, 52.11, 52.83, 55.48, 55.52, 59.28, 60.08, 68.58, 68.76, 68.82, 79.46, 80.03, 110.09, 110.73, 111.13, 126.11, 126.18, 126.37, 127.07, 146.81, 146.87, 147.93, 153.86, 154.30, 166.29, 166.78, 166.94, 167.06.

Method 2 Selective Hydrolysis and Decarboxylation of Protected Ester 2

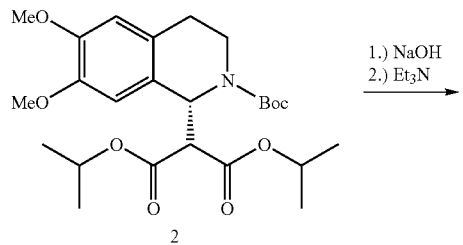

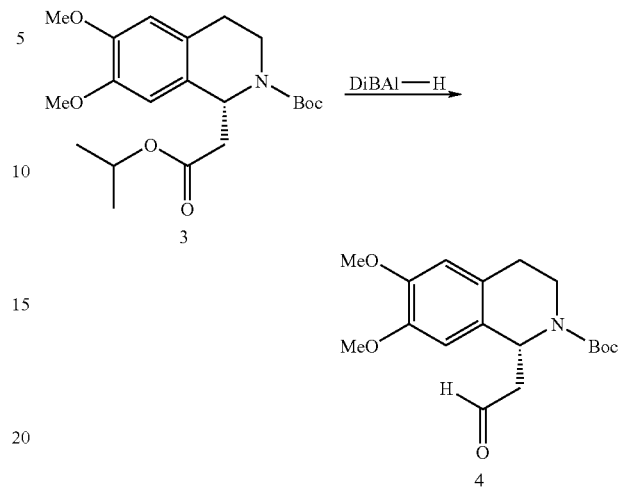

Method 3 Preparation of Aldehyde Compound 4

The starting material 2 was taken up in isopropanol to provide a 0.2 M solution of 2. To this solution was added 1M aqueous NaOH solution bringing the final concentration of the reaction mixture to 0.1M with respect to the malonate 2. The reaction mixture was heated to and maintained 70° C. for 22 min. (timing was started when the temperature of the reaction mixture temp exceeded 65° C.). Following the allotted time the reaction mixture was quickly cooled to 0° C. The reaction mixture carefully acidified with 2M aqueous HCl and extracted with three portions of dichloromethane. The combined organic extracts dried (Na$_2$SO$_4$), filtered and concentrated under reduced pressure. The isolated material was taken up in THF to provide a 0.1 M solution (based on the original quantity of 2 used in the reaction mixture) and triethylamine (1.0 eq) was added to the reaction mixture at room temperature. The reaction mixture was heated to its reflux temperature and maintained at this temperature for 90 min. The reaction mixture was concentrated under reduced pressure, dissolved in a minimal quantity of CH$_2$Cl$_2$ and was immediately purified by column chromatography on SiO$_2$ (15-40% EtOAc-hexanes; 40%, the eluant was monitored at 284 nm). The product 3 existed as a mixture of rotamers at room temperature and was a colorless foam 79%: $[\alpha]^{26}_D$ −82 (c 0.24, CH$_2$Cl$_2$); $^1$H NMR (CDCl$_3$) δ 1.19-1.25 (m, 6H), 1.43-1.49 (m, 9H), 2.58-2.69 (m, 2H), 2.70-2.77 (m, 1H), 2.78-2.92 (m, 1H), 3.13-3.43 (m, 1H), 3.81-3.85 (m, 6H), 3.86-4.01 (m, 1H), 4.91-5.05 (m, 1H), 5.38-5.61 (m, 1H), 6.56-6.61 (m, 1H), 6.64-6.70 (s, 1H); $^{13}$C NMR (CDCl$_3$) δ 21.75, 21.90, 27.93, 28.08, 28.44, 37.53, 38.75, 42.22, 42.81, 51.11, 51.87, 55.92, 56.02, 68.08, 79.74, 80.21, 109.60, 109.99, 111.44, 111.54, 126.28, 126.48, 128.54, 128.76, 147.51, 147.97, 154.39, 154.51, 170.36, 170.59; LRMS-(ESI+) calcd for (C$_{21}$H$_{31}$NO$_6$+H) ([M+H]$^+$ 394.22. found 394.16.

To a 0.12 M solution of the starting monoester (3, 1.0 eq.) in toluene at −78° C. was added a 1.5 M solution of DiBAl—H in hexanes (1.5 eq.) dropwise via a syringe pump. Following the addition the reaction mixture was stirred at −78° C. for 2 h. The reaction mixture was quenched by the addition of EtOAc and was then acidified with saturated aqueous citric acid solution. The reaction mixture was allowed to warm to room temperature and continue stirring for 30 min. The phases were separated, and the aqueous layer extracted with three portions of EtOAc. The combined organic extracts were washed with two portions of 2 M aqueous HCl solution, brine, dried (MgSO$_4$), filtered, and concentrated under reduced pressure. The crude product was subjected purification on SiO$_2$ (15-35% EtOAc-hexanes; Elution was observed at 285 nm and 228 nm). The isolated product aldehyde compound 4 was a colorless foam. The product existed as a 1:1 mixture of rotamers at room temperature 76%: $[\alpha]^{26}_D$ −116 (c 0.26, CH$_2$Cl$_2$); $^1$H NMR (CDCl$_3$) δ 1.40 (s, 9H), 2.58 (apparent t, J=3.8 Hz, 0.5H), 2.61 (apparent t, J=3.5 Hz, 0.5H), 2.68-2.88 (m, 3H), 3.02-3.27 (m, 1H), 3.78 (apparent s, 6H), 3.87-3.99 (m, 0.5H), 4.08-4.23 (m, 0.5H), 5.37-5.68 (m, 1H), 6.55 (s, 1H), 6.58 (s, 1H), 9.78 (s, 1H); $^{13}$C NMR (CDCl$_3$) δ 20.90, 28.02, 28.27, 37.23, 38.65, 49.29, 49.93, 51.12, 55.83, 55.96, 80.13, 80.64, 109.42, 109.52, 111.52, 126.34, 126.51, 127.78, 127.82, 147.72, 147.97, 153.85, 154.62, 200.08, 200.33.

Method 4 Reaction Of Aldehyde Compound 4 With Nucleophilic Alkenyl Species Derived From Alkenyl Iodide 5 With To Provide Allylic Alcohol 6

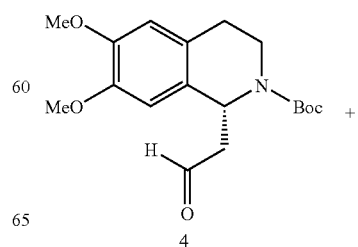

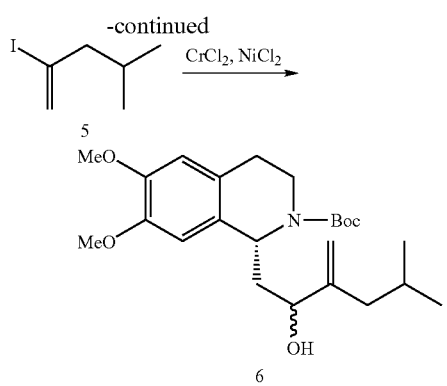

To a neat mixture of the alkenyl iodide 5 (1.0 eq) and the aldehyde compound 4 (1.0 eq.) at room temperature was added 2.65 eq. of chromium chloride doped with 0.5% NiCl$_2$ (w/w). The mixture was vortexed for about 2 min. to provide a homogeneous, green/grey paste and then stirred under nitrogen for an additional 10 min. after which time anhydrous DMF was added to bring the final reaction concentration to 0.36 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h. The aqueous layer was extracted with three portions of EtOAc, dried (MgSO$_4$), filtered, and the filtrate was concentrated under reduced pressure to provide a green oil. The crude material was subjected to column chromatography on SiO$_2$ (35% EtOAc-hexanes; elution was observed at 285 nm and 228 nm). The product allylic alcohol 6 was a pale yellow oil isolated in 53% yield as a mixture of diastereomers which was taken on to the next step without additional characterization or analysis.

Method 5 Reaction Of Aldehyde Compound 4 With Nucleophilic Alkenyl Species Derived From Alkenyl Iodide 7 With To Provide Allylic Alcohol 8

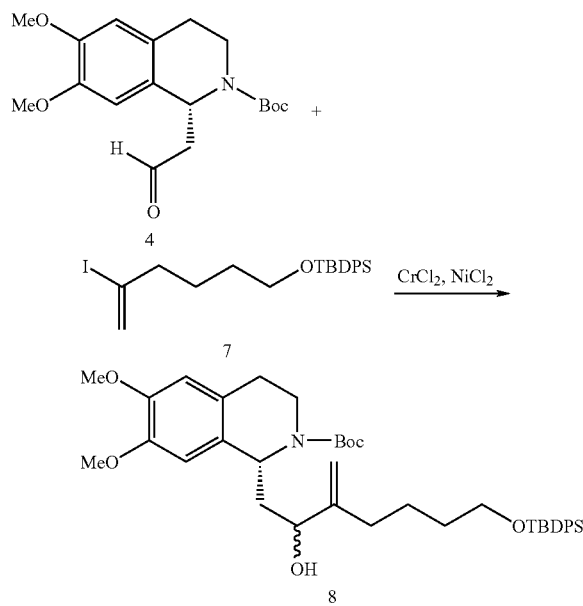

To a neat mixture of the alkenyl iodide 7 (1.0 eq) and the aldehyde compound 4 (1.25 eq.) at room temperature was added 2.5 eq. of chromium chloride doped with 0.5% NiCl$_2$ (w/w). The mixture was vortexed for about 2 min. to provide a homogeneous, green/grey paste and then stirred under nitrogen for an additional 10 min. after which time anhydrous DMF was added to bring the final reaction concentration to 0.32 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h. The aqueous layer was extracted with three portions of EtOAc, dried (MgSO$_4$), filtered, and the filtrate was concentrated under reduced pressure to provide a green oil. The crude material was subjected to column chromatography on SiO$_2$ (20% EtOAc-hexanes to 35% EtOAc-hexanes; elution was observed at 285 nm and 228 nm). The product allylic alcohol 8 was a pale yellow oil isolated in 54% yield as a mixture of diastereomers which was taken on to the next step without additional characterization or analysis.

Method 6 Reaction Of Aldehyde Compound 4 With Nucleophilic Alkenyl Species Derived From Alkenyl Iodide 9 With To Provide Allylic Alcohol 10

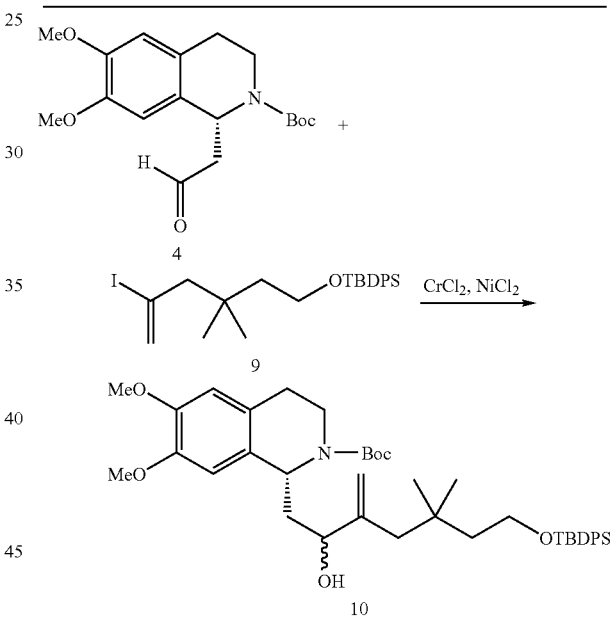

To a neat mixture of the alkenyl iodide 9 (1.5 eq) and the aldehyde 4 (1.0 eq.) at room temperature was added 2.5 eq. of chromium chloride doped with 0.5% NiCl$_2$ (w/w). The mixture was vortexed for about 2 min. to provide a homogeneous, green/grey paste and then stirred under nitrogen for an additional 10 min. after which time anhydrous DMF was added to bring the final reaction concentration to 0.36 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h. The aqueous layer was extracted with three portions of EtOAc, dried (MgSO$_4$), filtered, and the filtrate was concentrated under reduced pressure to provide a green oil. The crude material was subjected to column chromatography on SiO$_2$ (40% EtOAc-hexanes; elution was observed at 285 nm and 228 nm) to afford the product allylic alcohol 10 as a pale yellow oil that existed as a 1:1 mixture of diastereomers (47%): $^1$H NMR (CD$_2$Cl$_2$) δ 0.94-1.00 (m, 6H), 1.13-1.16 (m, 9H), 1.54-1.57 (m, 9H), 1.67-1.74 (m, 2H), 1.79-1.86 (m, 0.5H), 1.87-1.94 (m, 1H), 1.96-2.05 (m, 0.5H), 2.09-2.24 (m, 2H), 2.66-2.77 (m, 1H), 2.85-2.99 (m, 1H), 3.16-3.22 (m, 0.5H), 3.36-3.44 (m, 0.5H), 3.80-3.92 (m, 8H), 4.01-4.08 (m, 0.5H), 4.12-4.17 (m, 0.5H), 4.30-4.38 (m, 0.5H), 4.66-4.77 (m, 0.5H), 4.86-4.96 (m, 1H), 5.23-5.30 (m, 0.5H), 5.34-5.39 (m, 1H), 5.39-5.43 (m, 0.5H), 6.68-6.72 (m, 1H), 6.73-6.77 (m, 0.5H), 6.77-6.81 (m, 0.5H), 7.43-7.52 (m, 6H), 7.75-7.82 (m, 4H); $^{13}$C NMR (CD$_2$Cl$_2$) δ 19.12, 26.83, 27.33, 27.45, 27.54, 27.59, 28.29, 28.41, 33.46, 33.48, 38.30, 39.45, 43.64, 43.82, 44.93, 45.05, 45.48, 45.95, 50.95, 52.25, 55.89, 55.99, 56.01, 61.14, 69.99, 73.06, 80.03, 80.49, 110.21, 110.56, 111.87, 112.00, 112.02, 112.39, 125.92, 126.32, 126.35, 127.77, 129.57, 129.69, 130.17, 134.15, 135.68, 147.85, 147.88, 147.99, 148.11, 148.71, 149.59, 149.61, 155.79, 156.39.

Method 7 Oxidation Of Allylic Alcohol 6 To Provide First Intermediate 12

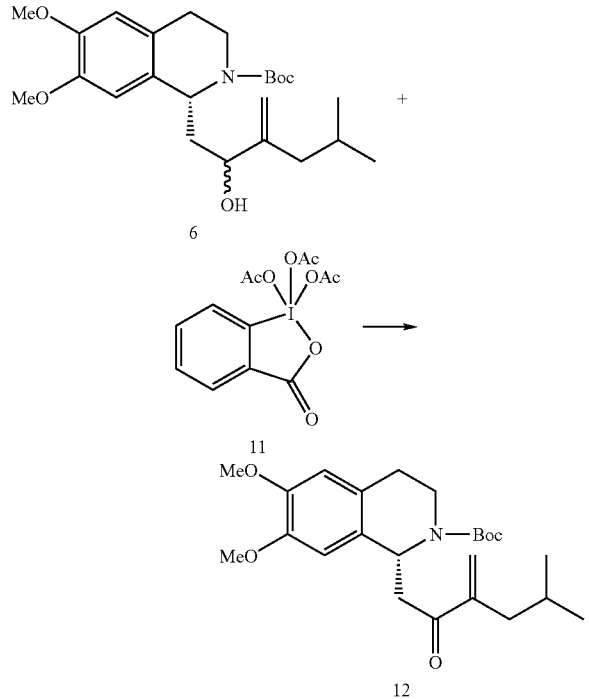

To a 0.1 M solution of allylic alcohol 6 (1.0 eq) in dichloromethane at 0° C. was added 1.1 eq. of the Dess-Martin reagent 11. The reaction mixture was allowed to stir, slowly warming to room temperature over 2.5 h. The reaction was quenched by the addition of saturated aqueous sodium bicarbonate solution and diluted with ethyl acetate. The organic and aqueous layers were partitioned and separated and the aqueous layer extracted with three additional portions of ethyl acetate. The combined organic extracts were washed with brine, dried (MgSO$_4$), filtered, and concentrated under reduced pressure. The crude material was purified by column chromatography on SiO$_2$ (10-30% EtOAc-hexanes, elution was observed at 285 nm and 228 nm). The product first intermediate 12 was a colorless, foul-smelling oil that existed at 26° C. as a 60:40 mixture of rotamers in solution (66%): $^1$H NMR (CDCl$_3$) δ 0.82 (apparent t, J=7.6 Hz, 6H), 1.42 (s, 9H), 1.70 (apparent sept, J=6.62 Hz, 1H), 2.08-2.15 (m, 1H), 2.15- 2.24 (m, 1H), 2.62-2.70 (m, 1H), 2.75-2.91 (m, 1H), 2.93-3.07 (m, 1H), 3.07-3.29 (m, 1.6H), 3.30-3.43 (m, 0.4H), 3.79 (s, 3H), 3.81 (s, 3.4H), 4.04-4.16 (m, 0.6H), 5.52-5.62 (m, 1H), 5.69 (s, 1H), 5.90 (s, 0.6H), 6.04 (s, 0.4H), 6.57 (s, 1H), 6.63 (s, 1H); $^{13}$C NMR (CDCl$_3$) δ 22.45, 27.04, 27.25, 28.11, 28.41, 38.01, 39.33, 40.39, 45.20, 45.90, 51.62, 55.92, 55.98, 79.75, 80.23, 109.85, 110.25, 110.28, 111.41, 125.65, 125.72, 126.26, 129.25, 147.57, 147.87, 148.16, 148.29, 148.35, 154.40, 154.51, 199.53; HRMS-(ESI+) calcd for (C$_{24}$H$_{35}$NO$_5$)+H) ([M+H]$^+$ 418.2594, found 418.2590.

Method 8 Oxidation Of Allylic Alcohol 8 To Provide First Intermediate 13

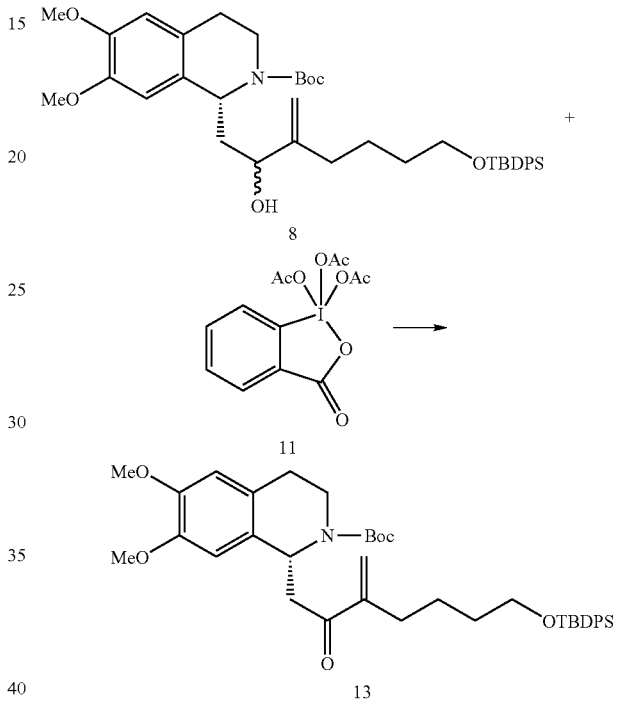

To a 0.1 M solution of 8 (1.0 eq) in dichloromethane at 0° C. was added 1.1 eq. of the Dess-Martin reagent 11. The reaction mixture was allowed to stir, slowly warming to room temperature over 2.5 h. The reaction was quenched by the addition of saturated aqueous sodium bicarbonate solution and diluted with dichloromethane. The organic and aqueous layers were partitioned and separated and the aqueous layer extracted with three additional portions of dichloromethane. The combined organic extracts were washed with brine, dried (MgSO$_4$), filtered, and concentrated under reduced pressure. The crude material was purified by column chromatography on SiO$_2$ (10-50% EtOAc-hexanes, elution was observed at 285 nm and 228 nm). The product first intermediate 13 was a colorless, oil that existed at 26° C. as a 50:50 mixture of rotamers in solution (82%): $^1$H NMR (CD$_2$Cl$_2$) δ 1.19 (s, 9H), 1.55 (s, 9H), 1.63-1.83 (m, 5H), 2.34-2.57 (m, 2H), 2.70-2.85 (m, 1H), 2.85-3.05 (m, 1H), 3.05-3.41 (m, 2.5H), 3.41-3.56 (m, 0.5H), 3.81-3.83 (m, 1H), 3.84 (s, 3H), 3.86 (s, 3H), 3.97-4.08 (m, 0.5H), 4.20-4.35 (m, 0.5H), 5.68 (apparent t, J=6.6 Hz, 1H), 5.87 (s, 1H), 6.09 (s, 0.5H), 6.19 (s, 0.5H), 6.71 (s, 1H), 6.76 (s, 1H), 7.45-7.60 (m, 6H), 7.77-7.95 (m, 4H); $^{13}$C NMR (CD$_2$Cl$_2$) δ 19.19, 24.66, 24.75, 26.83, 28.06, 28.28, 30.57, 32.43, 37.75, 39.20, 45.16, 45.66, 63.84, 79.46, 79.77, 110.21, 110.49, 111.81, 124.37, 124.67, 126.45, 127.76, 129.19, 129.68, 134.13, 135.61, 147.79, 148.19, 149.20, 154.09, 154.41, 199.15, 199.27; HRMS-(ESI+) calcd for $(C_{40}H_{53}NO_6Si+H)$ ([M+H]$^+$ 672.3720, found 672.3715.

Method 9 Oxidation Of Allylic Alcohol 10 To Provide First Intermediate 14

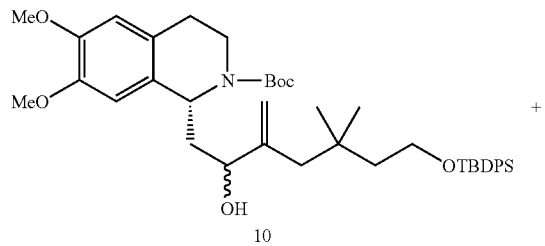

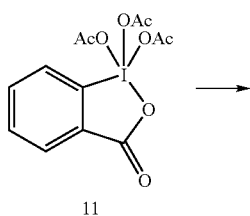

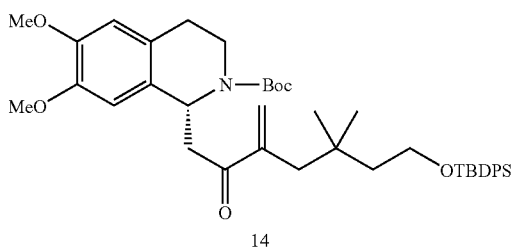

To a 0.1 M solution of allylic alcohol 10 (1.0 eq) in dichloromethane at 0° C. was added 1.1 eq. of the Dess-Martin reagent 11. The reaction mixture was allowed to stir, slowly warming to room temperature over 5 h. The reaction was quenched by the addition of saturated aqueous sodium bicarbonate solution and diluted with dichloromethane. The organic and aqueous layers were partitioned and separated and the aqueous layer extracted with three additional portions of dichloromethane. The combined organic extracts were washed with brine, dried (MgSO$_4$), filtered, and concentrated under reduced pressure. The crude material was purified by column chromatography on SiO$_2$ (10-50% EtOAc-hexanes, elution was observed at 285 nm and 228 nm). The product first intermediate 14 was a yellow foam that existed at 26° C. as a 50:50 mixture of rotamers in solution (93%): $^1$H NMR (CD$_2$Cl$_2$) δ 0.85 (s, 6H), 1.14 (s, 9H), 1.48-1.57 (m, 9H), 1.65 (t, J=7.3 Hz, 2H), 2.30-2.50 (m, 2H), 2.70-2.80 (m, 1H), 2.85-2.98 (m, 1H), 3.07-3.17 (m, 1H), 3.22-3.37 (m, 1.5H), 3.38-3.50 (m, 0.5H), 3.81 (s, 3H), 3.85 (s, 3H), 3.85-3.92 (m, 2H), 3.94-4.02 (m, 0.5H), 4.18-4.25 (m, 0.5H), 5.65-5.72 (m, 1H), 5.74 (s, 1H), 6.07 (s, 0.5H), 6.14 (s, 0.5H), 6.69 (s, 1H), 6.76 (s, 1H), 7.45-7.54 (m, 6H), 7.77-7.82 (m, 4H); $^{13}$C NMR (CD$_2$Cl$_2$) δ 19.09, 26.80, 26.92, 26.97, 28.13, 28.22, 28.28, 33.22, 37.94, 39.39, 41.79, 41.87, 44.49, 45.33, 46.02, 51.16, 51.44, 55.79, 55.83, 61.05, 79.47, 79.76, 110.18, 110.51, 111.74, 126.40, 127.26, 127.36, 127.76, 129.48, 129.69, 134.09, 135.66, 146.93, 147.06, 147.78, 148.10, 154.16, 154.47, 199.36; HRMS-(ESI+) calcd for $(C_{42}H_{57}NO_6Si-C_5H_9O_2(Boc)+H)$ ([M−Boc+H]$^+$ 600.3509, found 600.3496.

Method 10 Removal The Boc Protecting Group From First Intermediate 12 And Amino Cyclization Provide (+)-Tetrabenazine 15

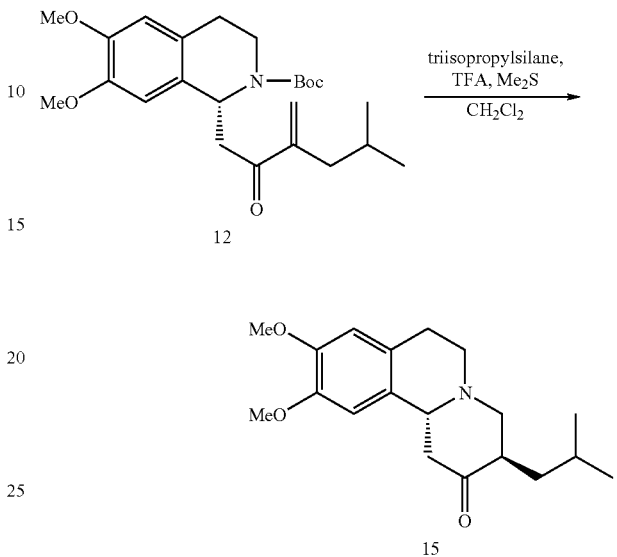

First intermediate 12 (1.0 eq) was dissolved in 10% Me$_2$S-dichloromethane to provide an 82 mM solution. The solution was cooled to 0° C. and triisopropylsilane (1.1 eq.) followed by TFA (precooled to 0° C.) was added to the reaction mixture to provide a final concentration of 41 mM. The reaction mixture was permitted to stir at 0° C. for 1 h. Following the allotted time the reaction mixture was quenched at 0° C. by the addition of saturated aqueous potassium carbonate solution and concentrated under reduced pressure to remove the majority of the dimethylsulfide. The mixture was extracted with five portions of dichloromethane, and the combined organic extracts were washed with brine, dried (MgSO$_4$), filtered and concentrated under reduced pressure to provide the crude product as a yellow solid. The crude product was recrystallized from 3.5% dimethoxyethane in hexanes. The resulting colorless crystals were washed with hexanes to provide pure (+)-tetrabenazine (15) 46%: mp 126.0° C. (3.5% DME-hexanes) (a crystal polymorph was observed at 116° C.); $[\alpha]^{26}_D$+37.2 (c 0.41, CH$_2$Cl$_2$); $^1$H NMR (CD$_2$Cl$_2$) δ 0.89 (apparent t, J=7.2 Hz, 6H), 0.98 (ddd, J=12, 6.0, 4.0 Hz, 1H), 1.59-1.68 (m, 1H), 1.74 (ddd, J=12, 5.9, 5.7 Hz, 1H), 2.32 (apparent t, J=11.7 Hz, 1H), 2.46 (apparent t, J=12.3 Hz, 1H), 2.55 (ddd, J=12, 10.0, 3.8 Hz, 1H), 2.65-2.73 (m, 2H), 2.83 (dd, J=5.5, 2.8 Hz, 1H), 2.97-3.07 (m, 1H), 3.07-3.14 (m, 1H), 3.25 (dd, J=9.7, 6.3 Hz, 1H), 3.47 (apparent d, J=12 Hz, 1H), 3.75 (s, 3H), 3.77 (s, 3H), 6.55 (s, 1H), 6.60 (s, 1H) $^{13}$C NMR (CD$_2$Cl$_2$) δ 21.98, 23.02, 25.51, 29.46, 35.16, 47.47, 47.63, 50.47, 55.87, 56.01, 61.47, 62.46, 108.46, 111.72, 126.37, 128.96, 147.65, 147.98, 209.72; HRMS-(ESI+) calcd for $(C_{19}H_{27}NO_3+H)$ ([M+H]$^+$ 318.2069, found 318.2082.

Method 11 Removal The Boc Protecting Group From
First Intermediate 13 And Amino Cyclization
Provide (+)-TBZ Compound 16

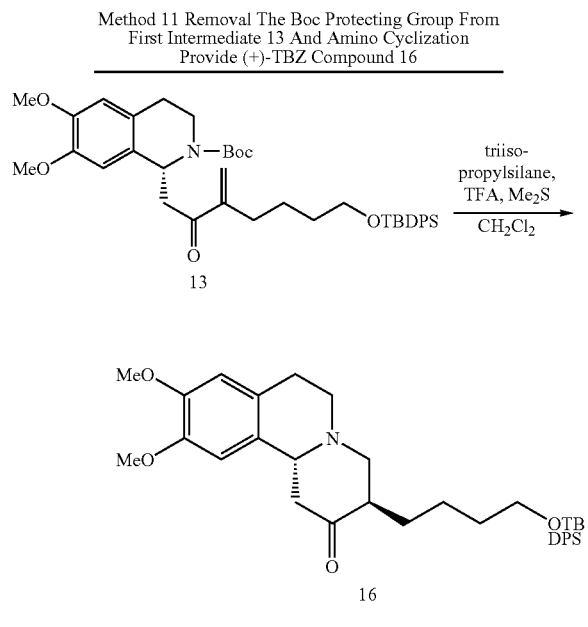

Method 12 Removal The Boc Protecting Group From
First Intermediate 14 And Amino Cyclization
Provide (+)-TBZ Compound 17

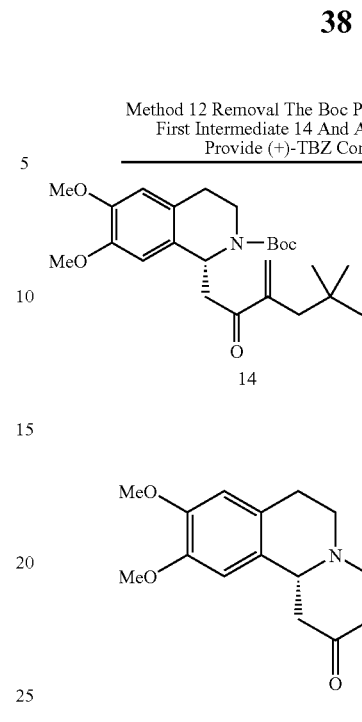

The first intermediate starting material 13 (1.0 eq) was dissolved in 10% Me$_2$S-dichloromethane to provide an 26 mM solution. The solution was cooled to 0° C. and triisopropylsilane (1.1 eq.) followed by TFA (precooled to 0° C.) was added to the reaction mixture to provide a final concentration of 13 mM. The reaction mixture was permitted to stir at 0° C. for 1 h. Following the allotted time the reaction mixture was quenched at 0° C. by the addition of saturated aqueous potassium carbonate solution and concentrated under reduced pressure to remove the majority of the dimethylsulfide. The mixture was extracted with five portions of dichloromethane, and the combined organic extracts were washed with brine, dried (MgSO$_4$), filtered and concentrated under reduced pressure to provide an orange oil. The isolated material was immediately subjected to purification by flash chromatography on SiO$_2$ (20-30% EtOAc-hexanes, elution was observed at 285 nm and 228 nm). The semipure product (existed as a mixture of diastereomers heavily favoring the desired product) was subjected to crystallization from 3.5% dimethoxyethane in hexanes over several days. The resulting colorless crystals were washed with hexanes to provide (+)-TBZ compound 16 as a single diastereomer 42%: $[\alpha]^{26}$D+40.1 (c 0.63, CH$_2$Cl$_2$); $^1$H NMR (CD$_2$Cl$_2$) δ 1.14 (s, 9H), 1.18-1.30 (m, 1H), 1.45-1.56 (m, 2H), 1.60-1.75 (m, 2H), 1.86-1.98 (m, 1H), 2.41 (apparent t, J=11.4 Hz, 1H), 2.47 (apparent t, J=12.6 Hz, 1H), 2.59-2.82 (m, 3H), 2.93 (dd, J=13.1, 2.8 Hz, 1H), 3.06-3.20 (m, 2H), 3.34 (dd, J=9.6, 6.1 Hz, 1H), 3.55 (apparent d, J=11.6 Hz, 1H), 3.78 (apparent t, J=6.3 Hz, 2H), 3.84 (s, 3H), 3.85 (s, 3H), 6.64 (s, 1H), 6.69 (s, 1H), 7.40-7.53 (m, 6H), 7.70-7.81 (m, 4H); $^{13}$C NMR (CD$_2$Cl$_2$) δ 19.14, 23.43, 25.98, 26.74, 29.47, 32.77, 47.55, 49.42, 50.44, 55.74, 55.86, 61.06, 62.36, 63.81, 108.31, 111.68, 126.31, 127.68, 128.91, 129.60, 134.15, 135.59, 147.59, 147.90, 209.36; HRMS-(ESI+) calcd for (C$_{35}$H$_{45}$NO$_4$Si+H) ([M+H]$^+$ 572.3196, found 572.3187.

The starting material 14 (1.0 eq) was dissolved in 10% Me$_2$S-dichloromethane to provide a 176 mM solution of the starting material. The solution was cooled to 0° C. and triisopropylsilane (1.1 eq.) followed by TFA (precooled to 0° C.) was added to the reaction mixture to provide a final concentration of 88 mM. The reaction mixture was permitted to stir at 0° C. for 1 h. Following the allotted time the reaction mixture was quenched at 0° C. by the addition of saturated aqueous potassium carbonate solution and concentrated under reduced pressure to remove the majority of the dimethylsulfide. The mixture was extracted with five portions of dichloromethane, and the combined organic extracts were washed with brine, dried (MgSO$_4$), filtered and concentrated under reduced pressure to provide a yellow foam. The crude product was purified by flash chromatography on SiO$_2$ (0.2% triethylamine-10% EtOAc-89.8% hexanes to 0.2% triethylamine-50% EtOAc-49.8% hexanes, elution was observed at 285 nm and 228 nm). The product (+)-TBZ compound 17 was a colorless foam consisting of only the desired diastereomer 73%: $^1$H NMR (CD$_2$Cl$_2$) δ 0.79 (dd, J=13.8, 3.8 Hz, 1H), 0.92 (s, 6H), 1.14 (s, 9H), 1.59-1.72 (m, 2H), 2.27 (dd, J=13.2, 5.1 Hz, 1H), 2.52-2.65 (m, 2H), 2.68-2.82 (m, 2H), 2.94 (dd, J=13.0, 3.0 Hz, 1H), 3.06-3.18 (m, 2H), 3.25 (dd, J=9.8, 6.3 Hz), 3.55 (dd, J=11.6, 1.8 Hz, 1H), 3.83-3.88 (m, 8H), 6.65 (s, 1H), 6.69 (s, 1H), 7.44-7.53 (m, 6H), 7.74-7.82 (m, 4H); $^{13}$C NMR (CD$_2$Cl$_2$) δ 19.09, 26.79, 27.10, 29.48, 32.31, 36.90, 44.38, 46.02, 47.45, 50.15, 55.77, 55.91, 61.09, 62.53, 63.50, 108.38, 111.75, 126.30, 127.74, 128.93, 129.67, 134.13, 135.65, 147.66, 147.98, 208.73; HRMS-(ESI+) calcd for (C$_{37}$H$_{49}$NO$_4$Si+H) ([M+H]$^+$ 600.3509, found 600.3499.

Method 13 Reduction of (+)-tetrabenazine 15 To a Diasteromeric Mixture of Dihydrotetrabenazine Compounds 18 and 19

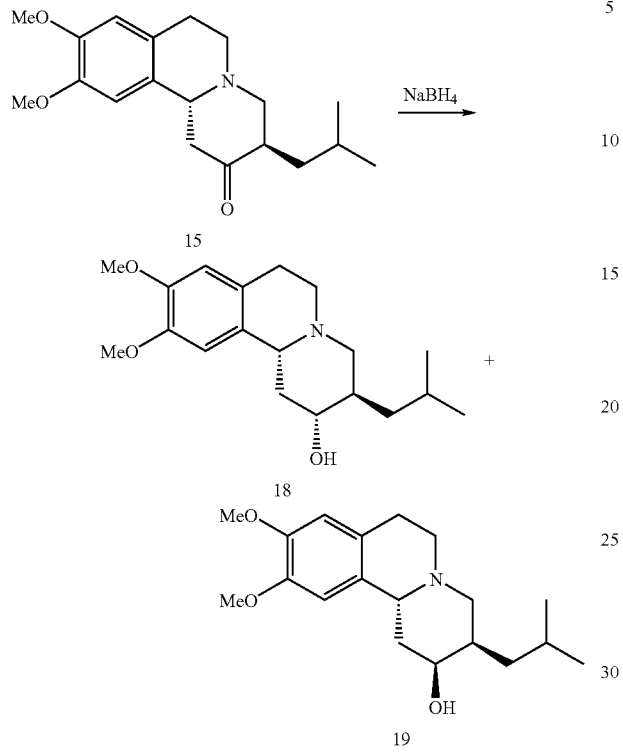

To a 0.11 M solution of (+)-TBZ (15) in ethanol at 0° C. was added NaBH$_4$ (2.85 eq). The reaction mixture was allowed to stir for 60 min. at room temperature. The solvent was carefully removed under reduced pressure, and the residue was taken up in dichloromethane and washed with three portions of saturated aqueous K$_2$CO$_3$. The aqueous washings were back extracted with two portions of dichloromethane. The combined organic extracts were dried (MgSO$_4$), filtered, and concentrated under reduced pressure to provide a colorless oil that crystallized on standing under high vacuum. Purification of the crude product was achieved by chromatography on SiO$_2$ (2.5-5% MeOH—CH$_2$Cl$_2$, elution was observed at 285 nm) UV active fractions were reanalyzed by TLC. Two products, 18 and 19, were isolated from this procedure. The major product 18 was a colorless solid 74%: $[\alpha]^{26}_D$ +48 (c 0.30, CH$_2$Cl$_2$) $^1$H NMR (CD$_2$Cl$_2$) δ 0.93 (d, J=6.6 Hz, 3H), 0.95 (d, J=6.6 Hz, 3H), 1.04 (ddd, J=14.6, 8.7, 4.3 Hz, 1H), 1.42 (dd, J=20.2, 11.4 Hz, 1H), 1.59 (ddd, J=13.7, 9.6, 3.3 Hz, 1H), 1.64-1.78 (m, 2H), 1.96 (apparent t, J=11.4 Hz, 1H), 2.27 (br s, 1H), 2.40-2.48 (m, 1H), 2.54 (ddd, J=12.3, 3.7, 2.3 Hz, 1H), 2.60-2.67 (m, 1H), 2.95-3.09 (m, 3H), 3.11 (apparent d, J=11.1 Hz, 1H), 3.35 (ddd, J=10.4, 10.4, 4.5 Hz, 1H), 3.80-3.81 (m, 6H), 6.60 (s, 1H), 6.69 (s, 1H); $^{13}$C NMR (CD$_2$Cl$_2$) δ 21.61, 24.02, 25.33, 29.30, 39.68, 40.81, 41.58, 51.83, 55.74, 55.91, 60.02, 60.92, 74.32, 108.42, 111.73, 126.68, 129.76, 147.35, 147.61; HRMS-(ESI+) calcd for (C$_{19}$H$_{29}$NO$_3$+H) ([M+H]$^+$ 320.2226, found 320.2242. The minor product 19 was a yellow oil 4%: $^1$H NMR (CD$_2$Cl$_2$) δ 0.94 (d, J=6.6 Hz, 3H), 0.96 (d, J=6.6 Hz, 3H), 1.13-1.20 (m, 1H), 1.24-1.34 (m, 2H), 1.60-1.77 (m, 2H), 1.89-2.00 (m, 1H) 2.36-2.44 (m, 2H), 2.53 (ddd, J=10.5, 10.5, 3.8 Hz, 1H), 2.58-2.70 (m, 2H), 2.91-2.98 (m, 1H), 2.98-3.09 (m, 1H), 3.48 (apparent d, J=11.6 Hz, 1H), 3.80-3.82 (apparent s, 6H), 4.07 (apparent d, J=3.1 Hz, 1H), 6.60 (s, 1H), 6.68 (s, 1H); $^{13}$C NMR (CD$_2$Cl$_2$) δ 22.74, 22.81, 24.87, 29.30, 37.83, 38.87, 39.42, 52.44, 55.76, 55.96, 56.32, 56.43, 67.88, 108.45, 111.78, 127.18, 130.38, 147.30, 147.54.

General Procedure for Making Ether Compounds Derived from DTBZ Having Structure V A mixture of DTBZ compound having structure V (1 equiv.) and NaH (5.0 equiv.) in DMF (0.1M) is heated at 60° C. for 3 hours (h). The mixture is cooled to 0° C. and the appropriate alkylating agent (e.g. a fluoroalkyl tosylate, an allyl halide, or a benzyloxyalkyl tosylate) is added and the mixture is allowed to warm to room temperature (RT). The reaction mixture is then heated at 60° C. for 14 h and cooled to RT. The reaction mixture is quenched by addition of water and extracted three times with an organic solvent (e.g. EtOAc, toluene, diethyl ether). The combined organic extracts are washed successively with water and brine, dried over a drying agent (e.g. Na$_2$SO$_4$, MgSO$_4$, CaCl$_2$), filtered and concentrated. The residue may be purified by chromatography to afford the product ether compound.

Method 14 Preparation of 2-Fluoroethyl 4-methylbenzenesulfonate 20

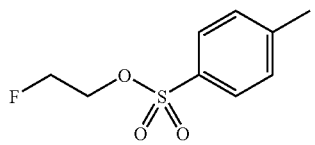

To a 0° C. solution of 2-fluoroethanol (1.0 g, 15.6 mmol) in pyridine (15 mL) was added tosyl chloride (6.5 g, 34.1 mmol) over 30 min. The reaction mixture was stirred at 0° C. for 4 h and quenched by adding ice-cold water and EtOAc. The layers separated and the organic layer was washed successively with water, 1M HCl (5×), saturated Na$_2$CO$_3$ and brine. The organic layer was dried over anhydrous Na$_2$SO$_4$, filtered and concentrated under reduced pressure. The residue was chromatographed on silica gel (12 g) using 5% to 40% EtOAc in hexane as the eluant to obtain fluorotosylate 20 (3.2 g, 95%) as a slightly yellow oil. $^1$H NMR (500 MHz, CDCl$_3$) δ 7.83 (d, J=10.0 Hz, 1H), 7.38 (d, J=10.0 Hz, 2H), 4.59 (dt, J=50.0 & 5.0 Hz, 2H), 4.28 (dt, J=30.0 & 5.0 Hz, 2H), 2.47 (s, 3H).

Method 15 Preparation of 3-Fluoropropyl 4-methylbenzenesulfonate 21

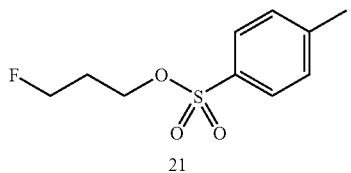

A mixture of 3-chloropropanol (2.5 mL, 30 mmol), KF (3.5 g, 60 mmol) and NaI (50 mg, 0.33 mmol) in ethylene glycol (10 mL) was placed in a round-bottom flask attached to a short-path distillation condenser. The mixture was heated at 130° C. and the resulting 3-fluoropropanol was collected as a colorless liquid. To a 0° C. solution of 3-fluoropropanol (600 mg, 7.68 mmol) in pyridine (8 mL) was added tosyl chloride (3.2 g, 16.78 mmol) over 30 min. The reaction mixture was stirred at 0° C. for 4 h and quenched by adding ice-cold water and EtOAc. The product fluorotosylate was purified as described in Method 14 above to afford compound 21 (1.2 g, 67%) as a slightly yellow oil. $^1$H NMR (500 MHz, CDCl$_3$) δ 7.83 (d, J=10.0 Hz, 1H), 7.38 (d, J=10.0 Hz, 2H), 4.59 (dt, J=50.0 & 5.0 Hz, 2H), 4.28 (dt, J=30.0 & 5.0 Hz, 2H), 2.47 (s, 3H).

Example 1

Preparation of Fluorinated Ether Compound 22

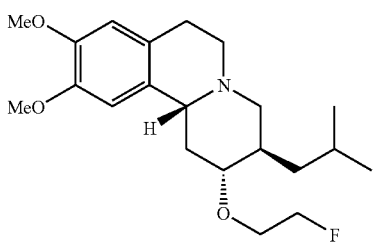

The general procedure for making ether compounds derived from DTBZ having structure V was used: DTBZ (18) (10 mg, 0.031 mmol), NaH (4 mg, 0.155 mmol) and 2-fluoroethyl 4-methylbenzenesulfonate (7 mg, 0.031 mmol) afforded 3 mg (27%) of the product fluorinated ether compound 22 having the 2R, 3R, 12R absolute stereochemistry shown as a yellow solid after flash chromatography on silica gel (4 g) using 1% to 2% MeOH in CH$_2$Cl$_2$ as the eluant. $^1$H NMR (500 MHz, CDCl$_3$) δ 6.69 (s, 1H), 6.61 (s, 1H), 4.65 (t, J=4.0 Hz, 1H), 4.56 (t, J=4.0 Hz, 1H), 3.89 (s, 3H), 3.87 (s, 3H), 3.07-3.18 (m, 3H), 3.01-3.04 (m, 1H), 2.59-2.69 (m, 2H), 2.48 (t, J=9.6 Hz, 1H), 2.01 (t, J=, 1H), 1.93-1.86 (m, 1H), 1.64-1.74 (m, 4H), 1.50 (q, J=9.0 Hz, 1H), 1.03 (ddd, J=14.6, 8.7 & 4.3 Hz, 1H), 0.95 (d, J=6.6 Hz, 3H), 0.93 (d, J=6.6 Hz, 3H). High Resolution Mass Spectrometry (HRMS) (ESI+) calculated for C$_{21}$H$_{32}$FNO$_3$ [M+H]$^+$ 366.2444, found 366.2441.

Example 2

Preparation of Fluorinated Ether Compound 23

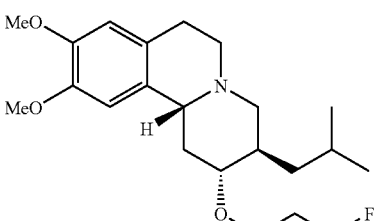

The general procedure for making ether compounds derived from DTBZ having structure V was used: DTBZ (18) (23 mg, 0.072 mmol), NaH (18 mg, 0.72 mmol) and 3-fluoropropyl 4-methylbenzenesulfonate (17 mg, 0.072 mmol) afforded 0.5 mg (2%) of the product fluorinated ether compound 23 having the 2R, 3R, 12R absolute stereochemistry shown as a yellow solid after preparative HPLC purification; HRMS (ESI+) calcd for C$_{22}$H$_{35}$FNO$_3$ [M]$^+$ 380.2601, found 380.2568.

Method 16 Preparation of Benzyloxypropyl DTBZ Ether 24

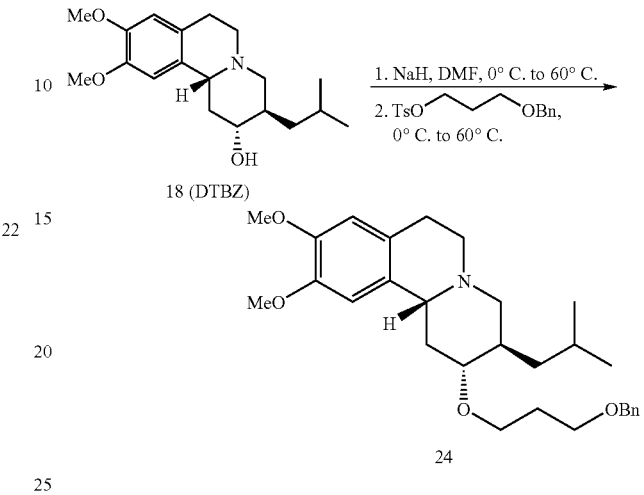

A mixture of DTBZ (18) (1 equiv.) and NaH (5.0 equiv.) in DMF (0.1M) is heated at 60° C. for 3 hours (h). The mixture is then cooled to 0° C. and treated with 3-benzyloxypropyl-tosylate and allowed to warm to room temperature. The reaction mixture is then heated at 60° C. for 14 h and cooled to ambient temperature. The reaction mixture is quenched by addition of water and the mixture is extracted three times with Et$_2$O (3×). The combined organic extracts are washed successively with water and brine, dried (Na$_2$SO$_4$), filtered and concentrated. The residue is purified by chromatography to afford the DTBZ ether compound having structure 24.

Method 17 Preparation of Hydroxypropyl DTBZ Ether 25

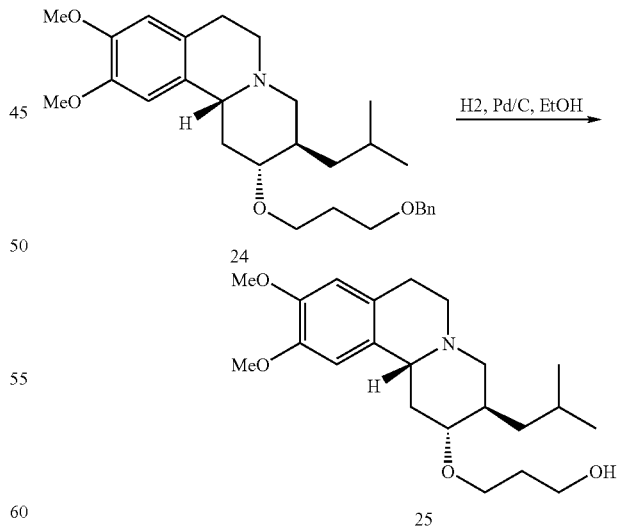

An ethanol (50 mL) solution of 100 mg benzyloxypropyl DTBZ ether 24 in a Parr bottle is first purged with argon gas and 5 weight percent palladium on carbon (10 mg) (Pd/C) is added. The Parr bottle is then attached to a Parr hydrogenation apparatus, is purged again with argon and then hydrogen gas.

Hydrogen pressure maintained at slightly above atmospheric pressure while the Parr bottle is gently rocked. The hydrogenolysis mixture is monitored periodically by thin layer chromatography (tlc). When tlc indicates complete removal of the benzyl group, the hydrogenolysis mixture is filtered through diatomaceous earth and the filtrate is concentrated under reduced pressure on a rotary evaporator to afford hydroxypropyl DTBZ ether 25.

Example 3

Preparation of Fluorophilic DTBZ Ether Tosylate 26

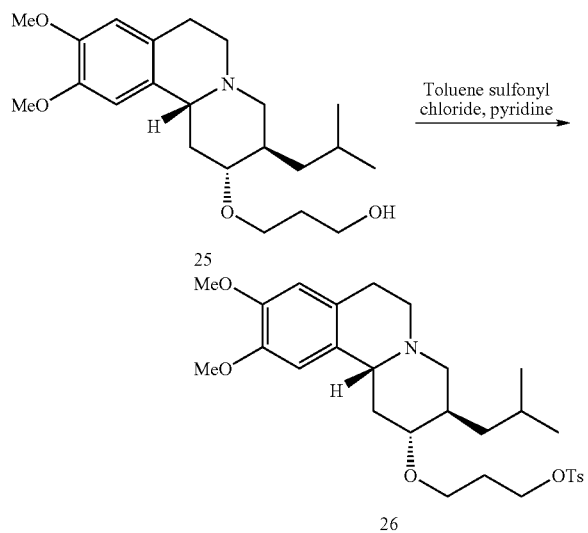

To a solution of 3-hydroxypropyl DTBZ ether derivative 25 (50 mg) in pyridine (1 mL) is added toluene sulfonyl chloride (tosyl chloride 1.5 equivalents) and the mixture is stirred at 0° C. and periodically monitored by tlc. When tlc indicates complete consumption of the starting 3-hydroxypropyl DTBZ ether, the reaction mixture is quenched by adding ice-cold water and EtOAc. The organic layer is washed successively with water, 1M HCl (5×), saturated $Na_2CO_3$ and brine. The organic layer is dried over anhydrous $Na_2SO_4$, filtered and concentrated under reduced pressure. The residue is chromatographed on silica gel to afford fluorophilic DTBZ ether tosylate 26.

Example 4

Preparation of PET Imaging Agent 27

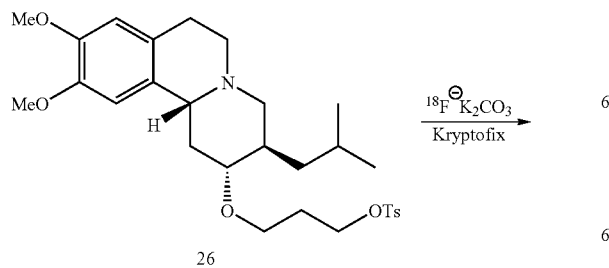

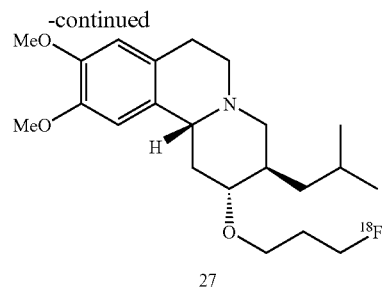

To a TEFLON-lined reaction vial contained in a shielded hood and fitted with a nitrogen purge inlet and magnetic spin bar, is added about 1 milliliter of an aqueous acetonitrile solution F-18 fluoride ion, potassium carbonate (about 1 mg), and Kryptofix 221 (about 10 mg). The vial is heated at 100° C. under a stream of nitrogen to effect the azeotropic removal of water. Additional dry acetonitrile (1 mL) is added and evaporated. This azeotropic drying protocol is repeated three times. After the final evaporation step a mixture of dimethyl formamide and acetonitrile (about 1 mL) containing DTBZ ether tosylate 26 (2 mg) is added and the vial is sealed. The reaction mixture is stirred and heated at 100° C. for 10 minutes and then is cooled to room temperature. The product mixture comprising the starting tosylate ether 26 and the product F-18 fluorinated ether compound 27 is diluted with water (10 mL) and applied to a Sep-Pak cartridge. The cartridge is then washed with water (3×) to remove unreacted fluoride ion and other water soluble components of the product mixture. The radiolabeled fluorinated ether compound 27 and starting tosylate 26 are then eluted from the cartridge with acetonitrile. Most of the acetonitrile is then evaporated and the residue is dissolved in aqueous acetonitrile and subjected to preparative reverse phase HPLC to afford an aqueous formulation comprising PET imaging agent 27.

Method 18 Preparation of Hydroxyethyl DTBZ Ether 28

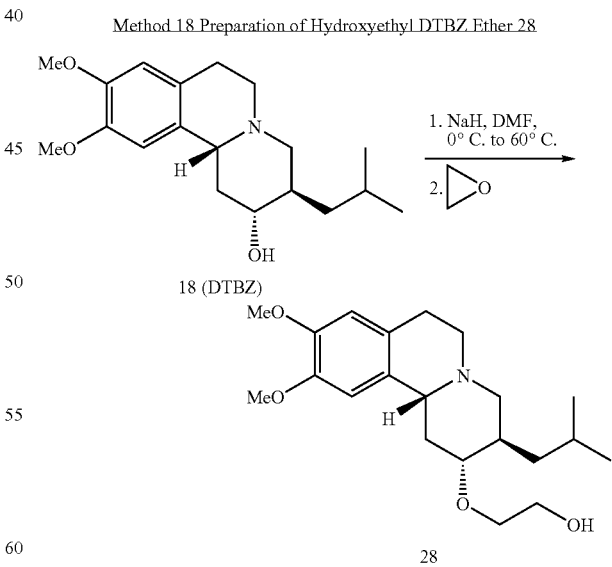

A mixture of DTBZ (18) (1 equiv.) and NaH (5.0 equiv.) in DMF (0.1M) is heated at 60° C. for 3 h. The mixture is then cooled to 0° C. and a solution containing ethylene oxide in tetrahydrofuran is added and allowed to warm to room temperature. The reaction mixture is then heated at 60° C. for 24 h and cooled to ambient temperature. The reaction mixture is quenched by addition of water and the mixture is extracted three times with Et$_2$O (3×). The combined organic extracts are washed successively with water and brine, dried (Na$_2$SO$_4$), filtered and concentrated. The residue is purified by chromatography to afford the hydroxyethyl DTBZ ether compound having structure 28.

Example 5

Preparation of Fluorophilic DTBZ Ether Tosylate 29

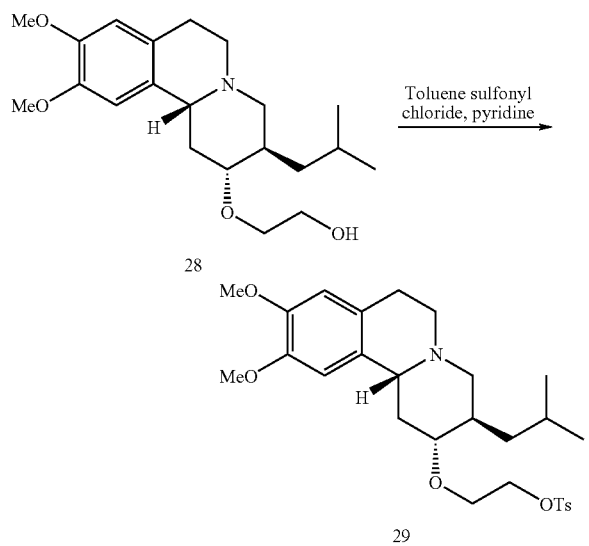

To a solution of 2-hydroxyethyl DTBZ ether derivative 28 (100 mg) in pyridine (2 mL) is added toluene sulfonyl chloride (tosyl chloride 1.5 equivalents) and the mixture is stirred at 0° C. and periodically monitored by tlc. When tlc indicates complete consumption of the starting 3-hydroxyethyl DTBZ ether, the reaction mixture is quenched by adding ice-cold water and EtOAc. The organic layer is washed successively with water, 1M HCl (5×), saturated Na$_2$CO$_3$ and brine. The organic layer is dried over anhydrous Na$_2$SO$_4$, filtered and concentrated under reduced pressure. The residue is chromatographed on silica gel to afford fluorophilic DTBZ ether tosylate 29 which may be further purified by recrystallization.

Example 6

Preparation of PET Imaging Agent 30

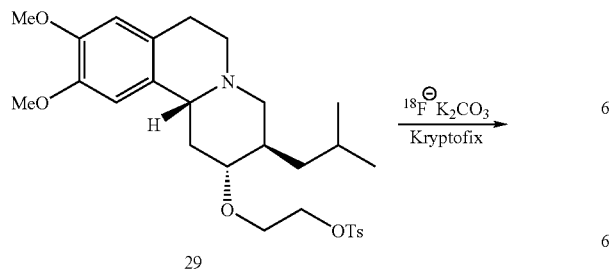

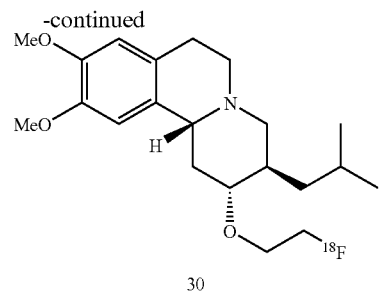

To a TEFLON-lined reaction vial contained in a shielded hood and fitted with a nitrogen purge inlet and magnetic spin bar, is added about 1 milliliter of an aqueous acetonitrile solution F-18 fluoride ion, potassium carbonate (about 1 mg), and Kryptofix 221 (about 10 mg). The vial is heated at 100° C. under a stream of nitrogen to effect the azeotropic removal of water. Additional dry acetonitrile (1 mL) is added and evaporated. This azeotropic drying protocol is repeated three times. After the final evaporation step a mixture of dimethyl formamide and acetonitrile (about 1 mL) containing DTBZ ether tosylate 29 (2 mg) is added and the vial is sealed. The reaction mixture is stirred and heated at 100° C. for 10 minutes and then is cooled to room temperature. The product mixture comprising the starting tosylate ether 29 and the product F-18 fluorinated ether compound 30 is diluted with water (10 mL) and applied to a Sep-Pak cartridge. The cartridge is then washed with water (3×) to remove unreacted fluoride ion and other water soluble components of the product mixture. The radiolabeled fluorinated ether compound 30 and starting tosylate 29 are then eluted from the cartridge with acetonitrile. Most of the acetonitrile is then evaporated and the residue is dissolved in aqueous acetonitrile and subjected to preparative reverse phase HPLC to afford an aqueous formulation comprising PET imaging agent 30.

Method 19 Alternate Preparation of PET Imaging Agent 30

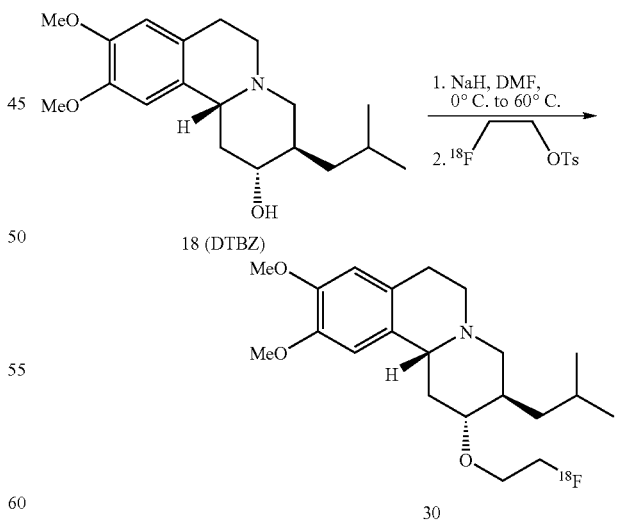

To a TEFLON-lined reaction vial contained in a shielded hood and fitted with a nitrogen purge inlet and magnetic spin bar, is added about 1 milliliter of an aqueous acetonitrile solution F-18 fluoride ion, potassium carbonate (about 1 mg), and Kryptofix 221 (about 10 mg). The vial is heated at 100° C.

under a stream of nitrogen to effect the azeotropic removal of water. Additional dry acetonitrile (1 mL) is added and evaporated. This azeotropic drying protocol is repeated three times. After the final evaporation step a mixture of dimethyl formamide and acetonitrile (about 1 mL) containing ethylene glycol bistosylate (2 mg) is added and the vial is sealed. The reaction mixture is stirred and heated at 100° C. for 10 minutes and then is cooled to room temperature. The product mixture comprising the starting bistosylate and the product F-18 fluorinated monotosylate is diluted with water (10 mL) and applied to a Sep-Pak cartridge. The cartridge is then washed with water (3×) to remove unreacted fluoride ion and other water soluble components of the product mixture. The radiolabeled fluorinated monotosylate and starting bistosylate are then eluted from the cartridge with acetonitrile. Most of the acetonitrile is then evaporated and the residue is dissolved in aqueous acetonitrile and subjected to preparative reverse phase HPLC to afford a purified F-18 fluorinated monotosylate. The purified F-18 fluorinated monotosylate is dried by azeotropic removal of water with acetonitrile. The dried F-18 fluorinated monotosylate is then reacted with approximately 2 mg of the sodium salt of DTBZ at 60° C. The product mixture comprising radiolabeled fluorinated ether compound 30 and the sodium salt of DTBZ is quenched with aqueous ammonium chloride and subjected to preparative HPLC to afford an aqueous formulation comprising PET imaging agent 30. Alternatively, the F-18 fluorinated monotosylate may be prepared and purified as described in *J. Label. Compd. Radiopharm.* 2006; 49: pp 177-195.

Method 20 Alternate Preparation of Hydroxypropyl DTBZ Ether 25

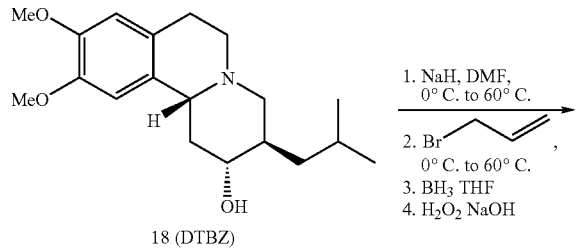

DTBZ (18) is reacted in dimethyl formamide (DMF) with sodium hydride and allyl bromide following the general procedure to afford DTBZ allyl ether 31 (See Method 21 below for structure) as a synthetic intermediate which is purified by column chromatography. The intermediate DTBZ allyl ether is treated overnight in tetrahydrofuran at room with one third of an equivalent of 1 molar borane (BH$_3$) in THF. Three equivalents of sodium perborate in a 1:1 mixture of THF: water is then added and the mixture is stirred overnight at room temperature. The reaction mixture is quenched by addition of water and extracted three times with Et$_2$O (3×). The combined organic extracts are washed successively with water and brine, dried (Na$_2$SO$_4$), filtered and concentrated. The residue is purified by chromatography to afford the 3-hydroxypropyl DTBZ ether compound having structure 25.

Method 21 Alternate Preparation of Hydroxyethyl DTBZ Ether 28

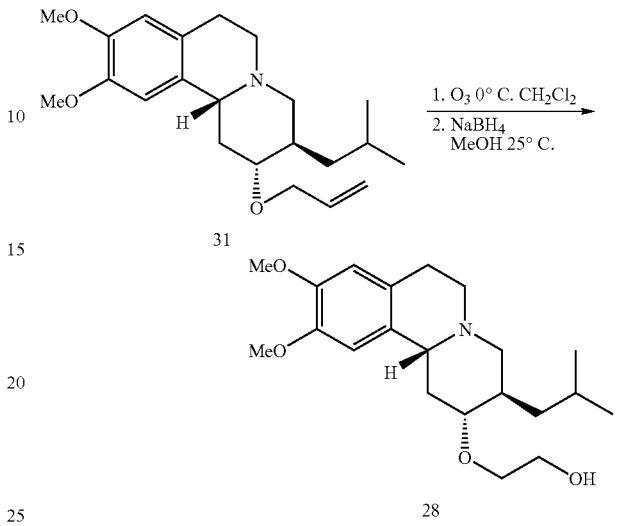

DTBZ allyl ether 31 (500 mg) is reacted in methylene chloride (CH$_2$Cl$_2$) at 0° C. with excess ozone for 1 hour. The reaction mixture is quenched at 0° C. by the addition by the addition of an aqueous solution of sodium borohydride followed by a volume of methanol equal to the volume of methylene chloride. The reaction mixture is allowed to warm to room temperature and the methanol and methylene chloride are removed on a rotary evaporator. The crude product is dissolved in ethyl acetate (EtOAc) and washed with saturated ammonium chloride solution, water, and brine, and then dried over sodium sulfate and filtered. The filtrate is concentrated under reduced pressure to provide hydroxyethyl DTBZ ether 28 which may be purified by column chromatography on silica gel.

Example 7

Preparation of PET Imaging Agent 33

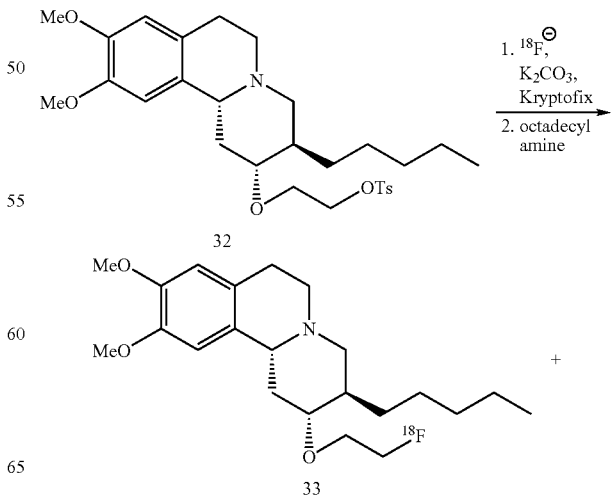

-continued

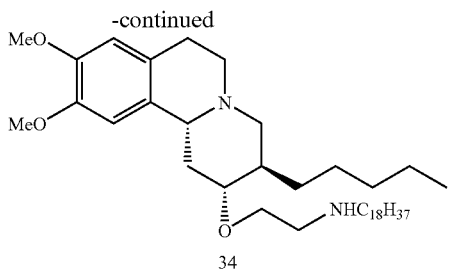

34

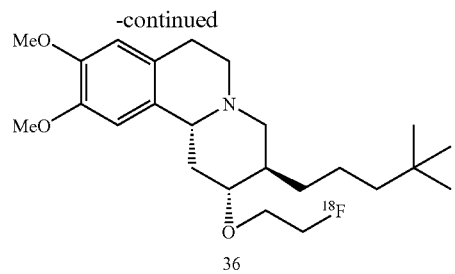

36

To a TEFLON-lined reaction vial contained in a shielded hood and fitted with a nitrogen purge inlet and magnetic spin bar, is added about 1 milliliter of an aqueous acetonitrile solution F-18 fluoride ion, potassium carbonate (about 1 mg), and Kryptofix 221 (about 10 mg). The vial is heated at 100° C. under a stream of nitrogen to effect the azeotropic removal of water. Additional dry acetonitrile (1 mL) is added and evaporated. This azeotropic drying protocol is repeated three times. After the final evaporation step a mixture of dimethyl formamide and acetonitrile (about 1 mL) containing ether tosylate 32 (2 mg, prepared analogously to compound 29) is added and the vial is sealed. The reaction mixture is stirred and heated at 100° C. for 10 minutes and then is cooled to room temperature. The product mixture comprising the starting tosylate ether 32 and the product F-18 fluorinated ether compound 33 is then treated with octadecyl amine 5 mg and potassium carbonate (2 mg) for 5 minutes at 60° C. to convert unreacted ether tosylate to the corresponding octadecyl amine 34. The product mixture is then diluted with water (10 mL) and applied to a Sep-Pak cartridge. The cartridge is then washed with water (3×) to remove unreacted fluoride ion and other water soluble components of the product mixture. The radiolabeled fluorinated ether compound 33 and the corresponding octadecyl amine adduct 34 are then eluted from the cartridge with acetonitrile. Most of the acetonitrile is then evaporated and the residue is dissolved in aqueous acetonitrile and subjected to preparative reverse phase HPLC to provide purified PET imaging agent 33.

Example 8

Preparation of PET Imaging Agent 36

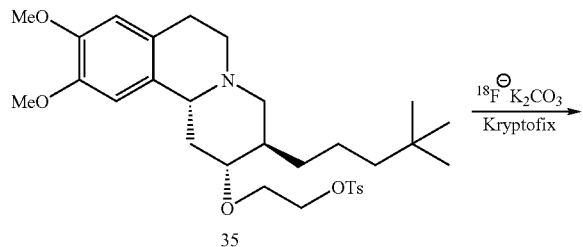

35

To a TEFLON-lined reaction vial contained in a shielded hood and fitted with a nitrogen purge inlet and magnetic spin bar, is added about 1 milliliter of an aqueous acetonitrile solution F-18 fluoride ion, potassium carbonate (about 1 mg), and Kryptofix 221 (about 10 mg). The vial is heated at 100° C. under a stream of nitrogen to effect the azeotropic removal of water. Additional dry acetonitrile (1 mL) is added and evaporated. This azeotropic drying protocol is repeated three times. After the final evaporation step a mixture of dimethyl formamide and acetonitrile (about 1 mL) containing ether tosylate 35 (2 mg, prepared analogously to compound 29) is added and the vial is sealed. The reaction mixture is stirred and heated at 100° C. for 10 minutes and then is cooled to room temperature. To the product mixture is added an amount of aminopropyl functionalized silica comprising approximately 10 equivalents of primary amine groups amine based on the number of moles of starting tosylate 35. The mixture is warmed to effect reaction between the aminopropyl functionalized silica and unreacted tosylate 35 and then filtered through a bed of diatomaceous earth. The bed of diatomaceous earth is rinsed with additional acetonitrile and the combined column effluent is concentrated to dryness in a sample preparation vial. Ethanol and water are added to the vial to provide an aqueous formulation of the PET imaging agent 36. The aqueous formulation comprising compound 36 is assayed by HPLC using a gamma ray detector capable of detecting fluorine-18 radiodecay.

Measurement of Binding Affinity of Fluorinated Ether Compounds to VMAT-2

VMAT-2 binding affinities were measured for fluorinated DTBZ ether compounds 22 and 23 provided by the present invention. VMAT-2 binding affinity measurements were carried out by Novascreen Biosciences Corporation (Hanover, Md., USA) using protocol Cat. No. 100-0751. Novascreen, Inc. is a commercial provider of biological assays for the pharmaceutical industry. Binding affinity data are presented in Table 9 and illustrate very high binding affinity for the fluorinated ether compounds of the present invention (compounds 22 and 23) relative to a DTBZ control (Comparative Example 1). The data obtained for fluorinated ether compounds 22 and 23 reveal an unexpected tolerance of replacement of the hydroxyl group at ring position-2 by a fluoroaliphatic radical, a structural change which combines a change in the size and lipophilicity of the group at ring position-2 in DTBZ with the uncertainty which arises whenever a hydrogen in a biologically active molecule is replaced by fluorine. In addition, the binding constants Ki expressed in nano-molar (nM) concentration units indicate a very high affinity of the fluorinated ether compounds of the present invention for the VMAT-2 biomarker.

TABLE 9

VMAT-2 Binding Affinity of Fluorinated ether compounds 22 and 23

| Example No. | Compound No. | Structure | Ki (nM) |
|---|---|---|---|
| Example 1 | 22 | MeO, MeO, H, O, F | 3.2 |
| Example 2 | 23 | MeO, MeO, H, O, F | 6.4 |
| Comparative Example 1 | DTBZ (18) | O, O, H, OH | 3.0 |

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all subranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

What is claimed is:

1. A fluorinated ether compound having structure I

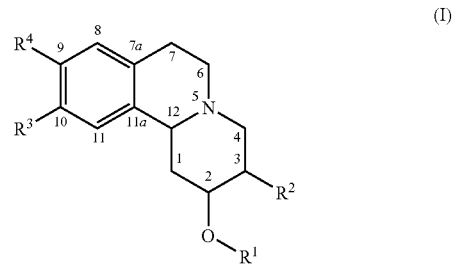

(I)

wherein $R^1$ is a $C_2$-$C_{10}$ fluorinated aliphatic radical; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

2. The fluorinated ether compound according to claim 1, comprising a fluorine-18 atom.

3. The fluorinated ether compound according to claim 1, comprising a fluorine-19 atom.

4. The fluorinated ether compound according to claim 1, which is enantiomerically enriched.

5. The fluorinated ether compound according to claim 1, which is comprised of at least 95 mole % of an enantiomer having the R configuration at ring position-12.

6. The fluorinated ether compound according to claim 1, which is comprised of at least 95 mole % of an enantiomer having the R configuration at ring position-3.

7. The fluorinated ether compound according to claim 1, in which the group —O—$R^1$ at ring position-2 has an anti configuration relative to the group $R^2$ at ring position-3.

8. The fluorinated ether compound according to claim 1, which comprises a mixture of diastereomers.

9. An enantiomerically enriched fluorinated ether compound comprising a principal component enantiomer having structure II

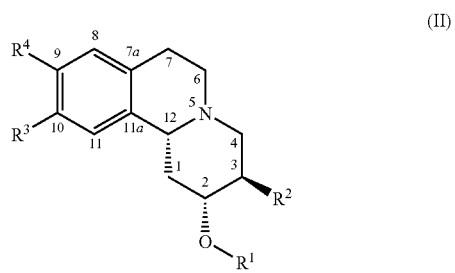

(II)

wherein $R^1$ is a $C_2$-$C_{10}$ fluorinated aliphatic radical; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

10. The enantiomerically enriched fluorinated ether compound according to claim 9, which is comprised of at least 80 mole % of an enantiomer having structure II.

11. The enantiomerically enriched fluorinated ether compound according to claim 9, which is comprised of at least 95 mole % of an enantiomer having structure II.

12. The enantiomerically enriched fluorinated ether compound according to claim 9, wherein $R^1$ is a $C_2$-$C_{10}$ fluorinated aliphatic radical; $R^2$ is isobutyl; and $R^3$ and $R^4$ are methoxy groups.

13. The enantiomerically enriched fluorinated ether compound according to claim 9, comprising a fluorine-18 atom.

14. The enantiomerically enriched fluorinated ether compound according to claim 13, said compound being comprised in a formulation suitable for administration to a patient.

15. The enantiomerically enriched fluorinated ether compound according to claim 13, said compound being comprised in a formulation suitable for use in PET imaging.

16. An enantiomerically enriched fluorinated ether compound comprising a principal component enantiomer having structure III

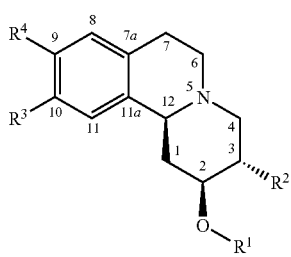

(III)

wherein $R^1$ is a $C_2$-$C_{10}$ fluorinated aliphatic radical; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

17. The enantiomerically enriched fluorinated ether compound according to claim 16, which is comprised of at least 80 mole % of an enantiomer having structure III.

18. The enantiomerically enriched fluorinated ether compound according to claim 16, which is comprised of at least 95 mole % of an enantiomer having structure III.

19. The enantiomerically enriched fluorinated ether compound according to claim 16, wherein $R^1$ is a $C_2$-$C_{10}$ fluorinated aliphatic radical; $R^2$ is isobutyl; and $R^3$ and $R^4$ are methoxy groups.

20. The enantiomerically enriched fluorinated ether compound according to claim 16, comprising a fluorine-18 atom.

21. A PET imaging agent comprising a fluorinated ether compound having structure I

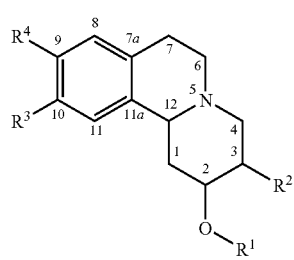

I wherein $R^1$ is a $C_2$-$C_{10}$ fluorinated aliphatic radical comprising at least one fluorine-18 atom; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

22. The PET imaging agent according to claim 21, comprising a fluorinated ether compound having structure IV

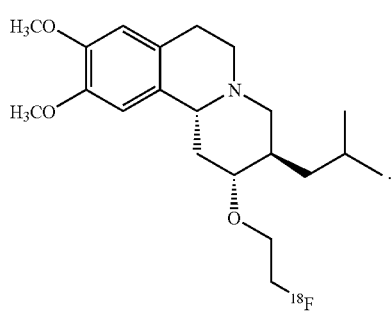

(IV)

23. A salt of a fluorinated ether compound having structure I

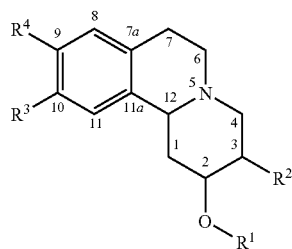

(I)

wherein $R^1$ is a $C_2$-$C_{10}$ fluorinated aliphatic radical; $R^2$ is a $C_1$-$C_{10}$ aliphatic radical, or a $C_3$-$C_{10}$ cycloaliphatic radical; $R^3$ is hydrogen or a $C_1$-$C_{10}$ aliphatic radical; and $R^4$ is hydrogen or a $C_1$-$C_{10}$ aliphatic radical.

* * * * *

UNITED STATES PATENT AND TRADEMARK OFFICE
CERTIFICATE OF CORRECTION

PATENT NO.       : 7,897,770 B2
APPLICATION NO.  : 11/923926
DATED            : March 1, 2011
INVENTOR(S)      : Amarasinghe et al.

It is certified that error appears in the above-identified patent and that said Letters Patent is hereby corrected as shown below:

On the Face Page, in Field (56), Under "FOREIGN PATENT DOCUMENTS", in Column 1, Line 4, delete "WO WO2005077946 A1 8/2005".

On the Face Page, in Field (56), Under "OTHER PUBLICATIONS", in Column 2, Line 7, delete "Dihyrotetrabenazine" and insert -- Dihydrotetrabenazine --, therefor.

On the Face Page, in Field (56), Under "OTHER PUBLICATIONS", in Column 2, Line 15, delete "Dihyrotetrabenazine" and insert -- Dihydrotetrabenazine --, therefor.

In Column 3, Line 43, delete "anthraceneyl" and insert -- anthracenyl --, therefor.

In Column 21, Line 54, delete "71 and insert -- 7i --, therefor.

In Column 42, Line 2, delete "$[M]^{+}$" and insert -- $[M+H]^{+}$ --, therefor.

In Column 21, Line 59, delete "71" and insert -- 7l --, therefor.

In Column 23, Line 30, delete "Ix" and insert -- IX --, therefor.

In Column 26, Line 62, delete "hydrolyis" and insert -- hydrolysis --, therefor.

In Column 28, Line 1, delete "Dihydrotetrrabenazine" and insert -- Dihydrotetrabenazine --, therefor.

In Column 29, Line 66, delete "394.22." and insert -- 394.22, --, therefor.

In Column 34, Line 10, delete "$(C_{24}H_{35}NO_5)+H)$" and insert -- $(C_{24}H_{35}NO_5+H)$ --, therefor.

In Column 37, Line 53, delete "$[\alpha]^{26}$ D" and insert -- $[\alpha]^{26}_D$ --, therefor.

Signed and Sealed this
Seventeenth Day of May, 2011

David J. Kappos
*Director of the United States Patent and Trademark Office*

In Column 42, Line 2, delete "$[M]^+$" and insert -- $[M+H]^+$ --, therefor.